US012286404B2

(12) United States Patent
Lapido et al.

(10) Patent No.: US 12,286,404 B2
(45) Date of Patent: Apr. 29, 2025

(54) SOLID STATE FORMS OF MITAPIVAT AND PROCESS FOR PREPARATION THEREOF

(71) Applicant: TEVA PHARMACEUTICALS INTERNATIONAL GMBH, Jona (CH)

(72) Inventors: Polina Lapido, Rishon LeZion (IL); Doron Rudik, Modi'in (IL); Ofir Shaul, Hod Hasharon (IL)

(*) Notice: Subject to any disclaimer, the term of this patent is extended or adjusted under 35 U.S.C. 154(b) by 456 days.

(21) Appl. No.: 17/794,693

(22) PCT Filed: Jan. 28, 2021

(86) PCT No.: PCT/US2021/015477
§ 371 (c)(1),
(2) Date: Jul. 22, 2022

(87) PCT Pub. No.: WO2021/154987
PCT Pub. Date: Aug. 5, 2021

(65) Prior Publication Data
US 2023/0098234 A1  Mar. 30, 2023

Related U.S. Application Data

(60) Provisional application No. 63/054,930, filed on Jul. 22, 2020, provisional application No. 63/028,028, filed on May 21, 2020, provisional application No. 63/013,715, filed on Apr. 22, 2020, provisional application No. 62/991,186, filed on Mar. 18, 2020, provisional application No. 62/991,172, filed on Mar. 18, 2020, provisional application No. 62/966,687, filed on Jan. 28, 2020.

(51) Int. Cl.
*C07D 215/36* (2006.01)

(52) U.S. Cl.
CPC ........ *C07D 215/36* (2013.01); *C07B 2200/13* (2013.01)

(58) Field of Classification Search
CPC ................... C07D 215/36; C07B 2200/13
See application file for complete search history.

(56) References Cited

U.S. PATENT DOCUMENTS 11,254,652 B2 * 2/2022 Sizemore ............. C07D 215/36

FOREIGN PATENT DOCUMENTS

WO    2011002817 A1    1/2011
WO    2019104134 A1    5/2019

OTHER PUBLICATIONS

International Search Report and Written Opinion of the International Searching Authority issued in corresponding application PCT/US2021/015477 mailed May 18, 2021 (19 pages).

* cited by examiner

*Primary Examiner* — Timothy R Rozof
(74) *Attorney, Agent, or Firm* — Carter, DeLuca & Farrell LLP

(57) ABSTRACT

Solid state forms of Mitapivat, Mitapivat hemisulfate, Mitapivat HCl, Mitapivat phosphate, Mitapivat hemisulfate: ascorbic acid and Mitapivat hemisulfate:adipic acid, processes for preparation thereof, pharmaceutical compositions thereof, and uses thereof are disclosed.

16 Claims, 23 Drawing Sheets

Figure 1: X-ray powder diffraction pattern (XRPD) of Mitapivat hemisulfate Form M1

Figure 2: X-ray powder diffraction pattern (XRPD) of Mitapivat hemisulfate Form M5

Figure 3: X-ray powder diffraction pattern (XRPD) of Mitapivat hemisulfate Form M6

Figure 4: X-ray powder diffraction pattern (XRPD) of Mitapivat Form B1

Figure 5: XRPD pattern of Mitapivat hemisulfate:ascorbic acid crystal Form ACC1

Figure 7: X-ray powder diffraction pattern (XRPD) of Mitapivat HCl Form I

Figure 8: X-ray powder diffraction pattern (XRPD) of Mitapivat HCl Form II

Figure 9: X-ray powder diffraction pattern (XRPD) of Mitapivat HCl Form III

Figure 10: X-ray powder diffraction pattern (XRPD) of Mitapivat HCl Form IV

SOLID STATE FORMS OF MITAPIVAT AND PROCESS FOR PREPARATION THEREOF

CROSS REFERENCE TO RELATED APPLICATIONS

This application is a National Stage of, and claims priority to and the benefit of, International Patent Application No. PCT/US2021/015477, filed Jan. 28, 2021, which, in turn, claims the benefit of and priority to, U.S. Provisional Application No. 62/966,687, filed Jan. 28, 2020; U.S. Provisional Application No. 62/991,172, filed Mar. 18, 2020; U.S. Provisional Application No. 62/991,186, filed Mar. 18, 2020; U.S. Provisional Application No. 63/013,715, filed Apr. 22, 2020; U.S. Provisional Application No. 63/028,028, filed May 21, 2020; and U.S. Provisional Application No. 63/054,930, filed Jul. 22, 2020, the entire disclosures of each of which are incorporated by reference herein.

FIELD OF THE DISCLOSURE

The present disclosure encompasses solid state forms of Mitapivat, Mitapivat salts and Mitapivat co-crystals, in embodiments crystalline polymorphs of Mitapivat, Mitapivat hemisulfate, Mitapivat HCl, Mitapivat phosphate, Mitapivat hemisulfate:ascorbic acid and Mitapivat hemisulfate;adipic acid, processes for preparation thereof, and pharmaceutical compositions thereof.

BACKGROUND OF THE DISCLOSURE

Mitapivat, N-[4-[4-(cyclopropylmethyl)piperazine-1-carbonyl]phenyl]quinoline-8-sulfonamide, has the following chemical structure:

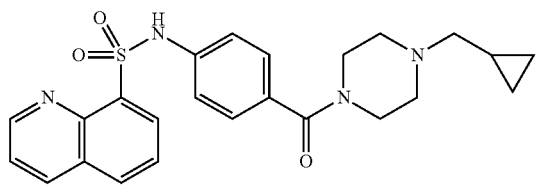 [SMILES: O=C(c1ccc(NS(=O)(=O)c2cccc3cccnc23)cc1)N1CCN(CC2CC2)CC1]

Mitapivat is a Pyruvate kinase R (PKR) activator and is developed by Agios for the treatment of Inborn errors of metabolism (IEMs) like Pyruvate kinase deficiencies, thalassemia and sickle cell disease.

The compound is described in International Publication No. WO 2011/002817. International Publication No. WO 2019/104134 describes amorphous and different crystalline forms of Mitapivat hemisulfate.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Mitapivat, Mitapivat hemisulfate or other salts of Mitapivat.

SUMMARY OF THE DISCLOSURE

The present disclosure provides crystalline polymorphs of Mitapivat, Mitapivat hemisulfate, Mitapivat HCl, Mitapivat phosphate, Mitapivat hemisulfate:ascorbic acid and Mitapivat hemisulfate:adipic acid, processes for preparation thereof, and pharmaceutical compositions thereof. These crystalline polymorphs can be used to prepare other solid state forms of Mitapivat, Mitapivat salts and their solid state forms, or other co-crystals of Mitapivat. The present disclosure also provides uses of the said solid state forms of Mitapivat, Mitapivat hemisulfate, Mitapivat HCl, Mitapivat phosphate, Mitapivat hemisulfate:ascorbic acid or Mitapivat hemisulfate;adipic in the preparation of other solid state forms of Mitapivat or salts or co-crystals thereof.

The present disclosure provides crystalline polymorphs of Mitapivat, Mitapivat hemisulfate, Mitapivat HCl, Mitapivat phosphate, Mitapivat hemisulfate:ascorbic acid or Mitapivat hemisulfate:adipic acid for use in medicine, including for the treatment of Inborn errors of metabolism (IEMs) like Pyruvate kinase deficiencies, thalassemia or sickle cell disease.

The present disclosure also encompasses the use of crystalline polymorphs of Mitapivat, Mitapivat hemisulfate, Mitapivat HCl, Mitapivat phosphate, Mitapivat hemisulfate: ascorbic acid or Mitapivat hemisulfate:adipic acid of the present disclosure for the preparation of pharmaceutical compositions and/or formulations.

In another aspect, the present disclosure provides pharmaceutical compositions comprising crystalline polymorphs of Mitapivat, Mitapivat hemisulfate, Mitapivat HCl, Mitapivat phosphate, Mitapivat hemisulfate:ascorbic acid or Mitapivat hemisulfate;adipic acid according to the present disclosure.

The present disclosure includes processes for preparing the above mentioned pharmaceutical compositions. The processes include combining any one or a combination of the crystalline polymorphs of Mitapivat, Mitapivat hemisulfate, Mitapivat HCl, Mitapivat phosphate, Mitapivat hemisulfate:ascorbic acid or Mitapivat hemisulfate:adipic acid with at least one pharmaceutically acceptable excipient.

The crystalline polymorph of Mitapivat, Mitapivat hemisulfate, Mitapivat HCl, Mitapivat phosphate, Mitapivat hemisulfate:ascorbic acid or Mitapivat hemisulfate:adipic acid as defined herein and the pharmaceutical compositions or formulations of the crystalline polymorph of Mitapivat, Mitapivat hemisulfate, Mitapivat HCl, Mitapivat phosphate, Mitapivat hemisulfate:ascorbic acid or Mitapivat hemisulfate:adipic acid may be used as medicaments, such as for the treatment of Inborn errors of metabolism (IEMs) like Pyruvate kinase deficiencies, thalassemia or sickle cell disease.

The present disclosure also provides methods of treating Inborn errors of metabolism (IEMs) like Pyruvate kinase deficiencies, thalassemia or sickle cell disease, by administering a therapeutically effective amount of any one or a combination of the crystalline polymorphs of Mitapivat, Mitapivat hemisulfate, Mitapivat HCl, Mitapivat phosphate, Mitapivat hemisulfate:ascorbic acid or Mitapivat hemisulfate:adipic acid of the present disclosure, or at least one of the above pharmaceutical compositions, to a subject suffering from Inborn errors of metabolism (IEMs) like Pyruvate kinase deficiencies, thalassemia or sickle cell disease, or otherwise in need of the treatment.

The present disclosure also provides uses of crystalline polymorphs of Mitapivat, Mitapivat hemisulfate, Mitapivat HCl, Mitapivat phosphate, Mitapivat hemisulfate:ascorbic acid or Mitapivat hemisulfate;adipic acid of the present disclosure, or at least one of the above pharmaceutical compositions, for the manufacture of medicaments for treating e.g., Inborn errors of metabolism (IEMs) like Pyruvate kinase deficiencies, thalassemia or sickle cell disease.

DETAILED DESCRIPTION OF THE DISCLOSURE

Figure 1:
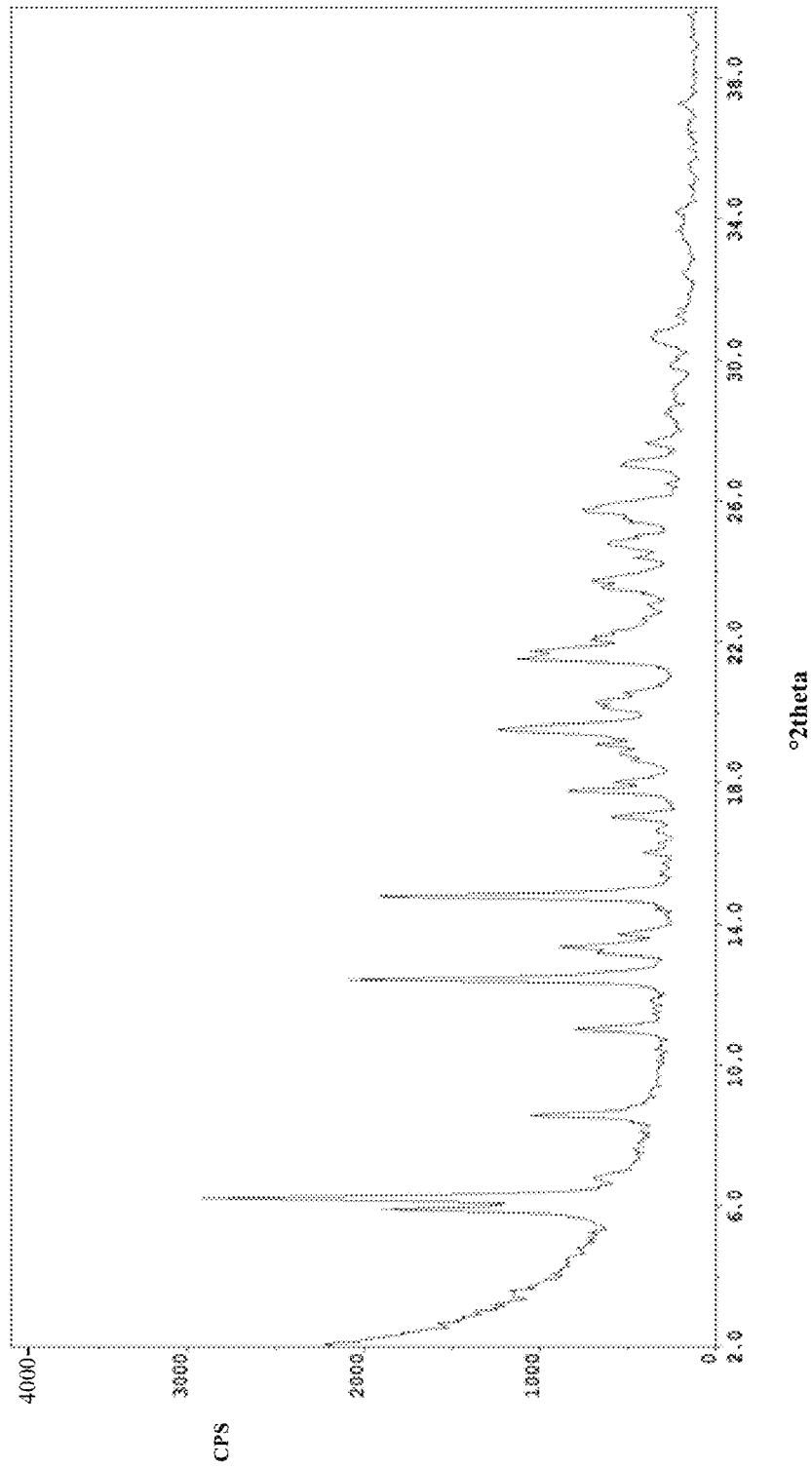
FIG. 1 shows a characteristic X-ray powder diffraction pattern (XRPD) of Mitapivat hemisulfate Form M1.

The present disclosure encompasses solid state forms of Mitapivat, Mitapivat salts and Mitapivat co-crystals, including crystalline polymorphs of Mitapivat, Mitapivat hemisulfate, Mitapivat HCl, Mitapivat phosphate, Mitapivat hemisulfate:ascorbic acid and Mitapivat hemisulfate;adipic acid, processes for preparation thereof, and pharmaceutical compositions thereof.

Solid state properties of Mitapivat, Mitapivat salts or Mitapivat co-crystals and crystalline polymorphs thereof can be influenced by controlling the conditions under which Mitapivat, Mitapivat salts or Mitapivat co-crystals and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Mitapivat, Mitapivat hemisulfate, Mitapivat HCl, Mitapivat phosphate, Mitapivat hemisulfate:ascorbic acid or Mitapivat hemisulfate:adipic acid described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Mitapivat, Mitapivat hemisulfate, Mitapivat HCl, Mitapivat phosphate, Mitapivat hemisulfate: ascorbic acid or Mitapivat hemisulfate:adipic acid, respectively. In some embodiments of the disclosure, the described crystalline polymorph of Mitapivat, Mitapivat hemisulfate, Mitapivat HCl, Mitapivat phosphate, Mitapivat hemisulfate: ascorbic acid or Mitapivat hemisulfate:adipic acid may contain from about 1% to about 20% (w/w), from about 5% to about 20% (w/w), or from about 5% to about 10% (w/w) of one or more other crystalline polymorph of the same Mitapivat, Mitapivat hemisulfate, Mitapivat HCl, Mitapivat phosphate, Mitapivat hemisulfate:ascorbic acid or Mitapivat hemisulfate:adipic acid, respectively.

Depending on which other crystalline polymorphs a comparison is made to, the crystalline polymorphs of Mitapivat, Mitapivat hemisulfate, Mitapivat HCl, Mitapivat phosphate, Mitapivat hemisulfate:ascorbic acid or Mitapivat hemisulfate:adipic acid of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Mitapivat, Mitapivat hemisulfate, Mitapivat HCl, Mitapivat phosphate, Mitapivat hemisulfate:ascorbic acid or Mitapivat hemisulfate;adipic acid referred to herein as being characterized by graphical data "as depicted in" or "as substantially depicted in" a Figure will thus be understood to include any crystal forms of Mitapivat, Mitapivat hemisulfate, Mitapivat HCl, Mitapivat phosphate, Mitapivat hemisulfate:ascorbic acid or Mitapivat hemisulfate;adipic acid characterized with the graphical data having such small variations, as are well known to the skilled person, in comparison with the Figure.

As used herein, and unless stated otherwise, the term "anhydrous" in relation to crystalline forms of Mitapivat, Mitapivat hemisulfate, Mitapivat HCl, Mitapivat phosphate, Mitapivat hemisulfate:ascorbic acid or Mitapivat hemisulfate:adipic acid, relates to a crystalline form of Mitapivat, Mitapivat hemisulfate, Mitapivat HCl, Mitapivat phosphate, Mitapivat hemisulfate:ascorbic acid or Mitapivat hemisulfate:adipic acid which does not include any crystalline water (or other solvents) in a defined, stoichiometric amount within the crystal. Moreover, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

"Co-crystal" as used herein is defined as a crystalline material including two or more molecules in the same crystalline lattice and associated by non-ionic and non-covalent bonds. In some embodiments, the co-crystal includes two molecules, which are in natural state. In an embodiment the molar ratio between the active pharmaceutical ingredient Mitapivat hemisulfate and the coformer ascorbic acid is between 1:1.5 and 1.5:1, preferably between 1:1.25 and 1.25:1, in other embodiments about 1:1. In another embodiment the molar ratio between the active pharmaceutical ingredient Mitapivat hemisulfate and the coformer ascorbic acid is between 1:0.7 and 1:0.3, in other embodiment about 1:0.5.

As used herein, crystalline Mitapivat hemisulfate:ascorbic acid is a distinct molecular species. Mitapivat hemisulfate:ascorbic acid may be a co-crystal of Mitapivat hemisulfate and ascorbic acid.

In a further embodiment the molar ratio between the active pharmaceutical ingredient Mitapivat hemisulfate and the coformer adipic acid is between 1:1.5 and 1.5:1, preferably between 1:1.25 and 1.25:1, in other embodiments about 1:1. In another embodiment the molar ratio between the active pharmaceutical ingredient Mitapivat hemisulfate and the coformer adipic acid is between 1:0.7 and 1:0.3, in other embodiment about 1:0.5. In an embodiment the molar ratio between the active pharmaceutical ingredient Mitapivat hemisulfate and the coformer adipic acid is 1:0.5.

As used herein, crystalline Mitapivat hemisulfate:adipic acid is a distinct molecular species. Mitapivat hemisulfate:adipic acid may be a co-crystal of Mitapivat hemisulfate and adipic acid.

As used herein, the term "isolated" in reference to crystalline polymorph of Mitapivat, Mitapivat hemisulfate, Mitapivat HCl, Mitapivat phosphate, Mitapivat hemisulfate:ascorbic acid or Mitapivat hemisulfate:adipic acid of the present disclosure corresponds to a crystalline polymorph of Mitapivat, Mitapivat hemisulfate, Mitapivat HCl, Mitapivat phosphate, Mitapivat hemisulfate:ascorbic acid or Mitapivat hemisulfate:adipic acid that is physically separated from the reaction mixture in which it is formed.

As used herein, unless stated otherwise, the XRPD measurements are taken using copper K$\alpha$ radiation wavelength 1.5418 Å. XRPD peaks reported herein are measured using CuK $\alpha$ radiation, $\lambda$=1.5418 Å, typically at a temperature of 25±3° C.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure includes a crystalline polymorph of Mitapivat hemisulfate, designated Form M1. The crystalline Form M1 of Mitapivat hemisulfate may be characterized by data selected from one or more of the following: an X-ray powder diffraction pattern substantially as depicted in FIG. 1; an X-ray powder diffraction pattern having peaks at 5.9, 6.2, 11.0, 12.4, and 14.7 degrees 2-theta±0.2 degrees 2-theta; and combinations of these data. Crystalline Form M1 of Mitapivat hemisulfate may be further characterized by an X-ray powder diffraction pattern having peaks at 5.9, 6.2, 11.0, 12.4, and 14.7 degrees 2-theta±0.2 degrees 2-theta, and also having any one, two, three, four or five additional peaks selected from 8.5, 13.3, 17.8, 19.5, and 21.5 degrees 2-theta±0.2 degrees 2-theta.

In one embodiment of the present disclosure, crystalline Form M1 of Mitapivat hemisulfate is isolated.

Crystalline Form M1 of Mitapivat hemisulfate may be anhydrous, hydrate or solvate form.

Crystalline Form M1 of Mitapivat hemisulfate may be characterized by each of the above characteristics alone or by all possible combinations, e.g., an XRPD pattern having peaks at 5.9, 6.2, 11.0, 12.4, and 14.7 degrees 2-theta±0.2 degrees 2-theta; an XRPD pattern as depicted in FIG. 1, and combinations thereof.

Figure 2:
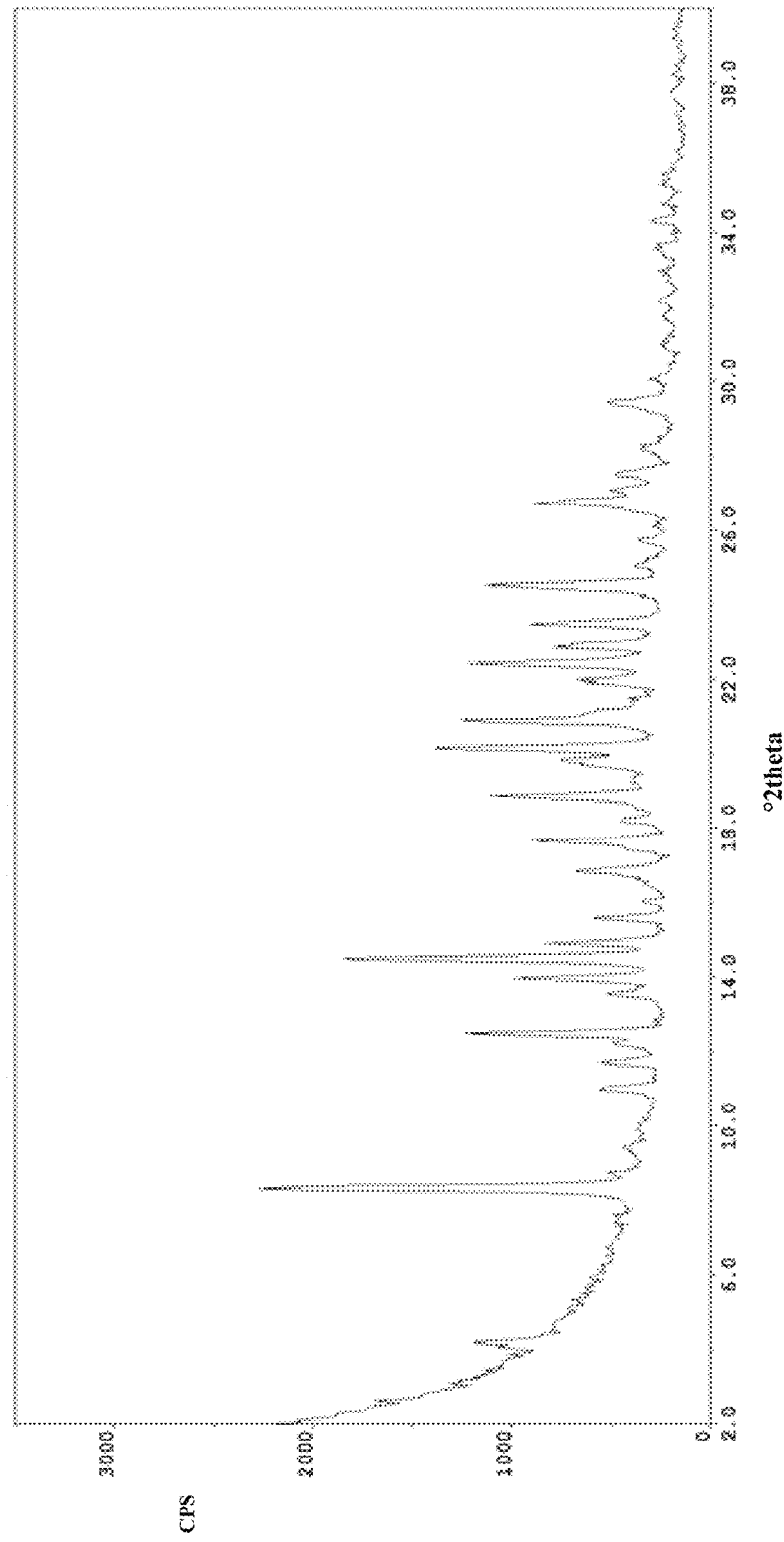
FIG. 2 shows a characteristic XRPD of Mitapivat hemisulfate Form M5.

The present disclosure includes a crystalline polymorph of Mitapivat hemisulfate, designated Form M5. The crystalline Form M5 of Mitapivat hemisulfate may be characterized by data selected from one or more of the following: an X-ray powder diffraction pattern substantially as depicted in FIG. 2; an X-ray powder diffraction pattern having peaks at 8.3, 12.5, 14.5, 20.1, and 22.4 degrees 2-theta±0.2 degrees 2-theta; and combinations of these data.

Crystalline Form M5 of Mitapivat hemisulfate may be further characterized by an X-ray powder diffraction pattern having peaks at 8.3, 12.5, 14.5, 20.1, and 22.4 degrees 2-theta±0.2 degrees 2-theta, and also having any one, two, three, four or five additional peaks selected from 4.2, 14.0, 15.6, 16.8, and 20.9 degrees 2-theta±0.2 degrees 2-theta.

In one embodiment of the present disclosure, crystalline Form M5 of Mitapivat hemisulfate is isolated.

Crystalline Form M5 of Mitapivat hemisulfate may be anhydrous, hydrate or solvate form.

Crystalline Form M5 of Mitapivat hemisulfate may be characterized by each of the above characteristics alone or by all possible combinations, e.g., an XRPD pattern having peaks at 8.3, 12.5, 14.5, 20.1, and 22.4 degrees 2-theta±0.2 degrees 2-theta; an XRPD pattern as depicted in FIG. 2, and combinations thereof.

Figure 3:
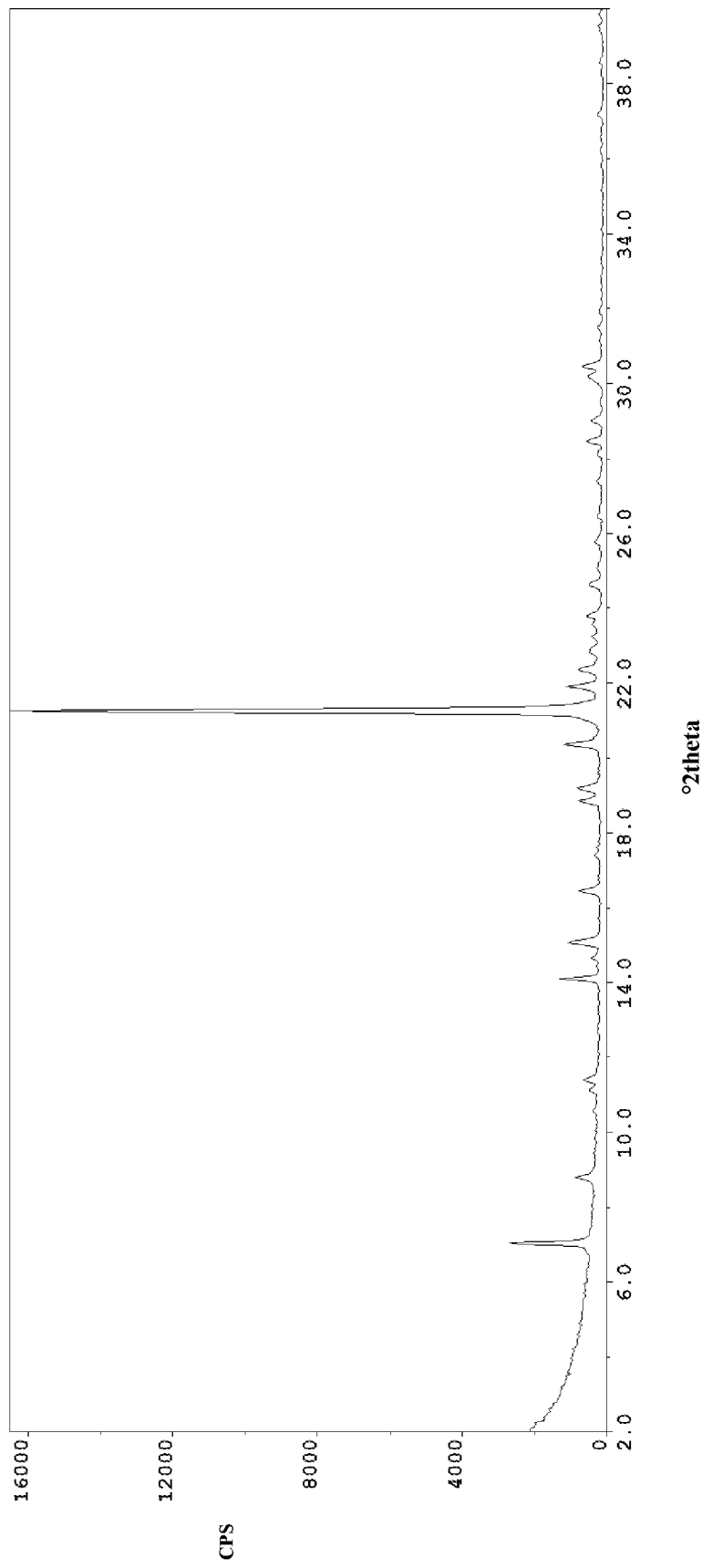
FIG. 3 shows a characteristic XRPD of Mitapivat hemisulfate Form M6.

The present disclosure includes a crystalline polymorph of Mitapivat hemisulfate, designated Form M6. The crystalline Form M6 of Mitapivat hemisulfate may be characterized by data selected from one or more of the following: an X-ray powder diffraction pattern substantially as depicted in FIG. 3; an X-ray powder diffraction pattern having peaks at 7.0, 14.7, 15.1, 20.4, and 21.3 degrees 2-theta±0.2 degrees 2-theta; and combinations of these data.

Crystalline Form M6 of Mitapivat hemisulfate may be further characterized by an X-ray powder diffraction pattern having peaks at 7.0, 14.7, 15.1, 20.4, and 21.3 degrees 2-theta±0.2 degrees 2-theta, and also having any one, two, three, four or five additional peaks selected from 8.8, 16.5, 19.2, 21.9, and 22.4 degrees 2-theta±0.2 degrees 2-theta.

Figure 12:
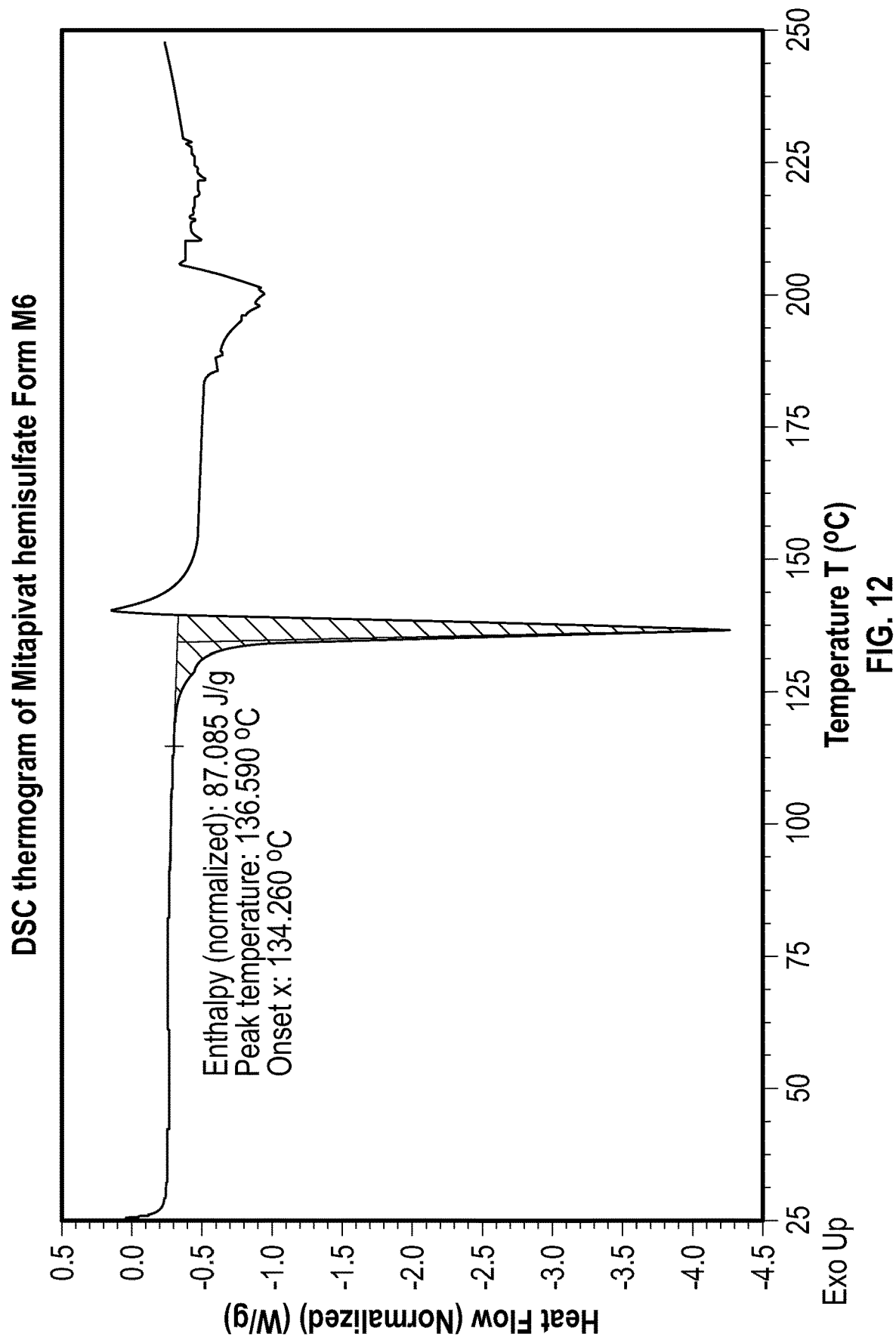
FIG. 12 shows a characteristic DSC thermogram of Mitapivat hemisulfate Form M6.

Crystalline Form M6 of Mitapivat hemisulfate may alternatively or additionally be characterized a DSC thermogram as depicted in FIG. 12; Crystalline Form M6 shows a melting endothermic peak at about 136.6° according to DSC thermogram.

In one embodiment of the present disclosure, crystalline Form M6 of Mitapivat hemisulfate is isolated.

Crystalline Form M6 of Mitapivat hemisulfate may be anhydrous, hydrate or solvate form. Crystalline Form M6 of Mitapivat hemisulfate may be a DMSO solvate.

Crystalline Form M6 of Mitapivat hemisulfate may be characterized by each of the above characteristics alone or by all possible combinations, e.g., an XRPD pattern having peaks at 7.0, 14.7, 15.1, 20.4, and 21.3 degrees 2-theta±0.2 degrees 2-theta; an XRPD pattern as depicted in FIG. 3, and combinations thereof.

Figure 4:
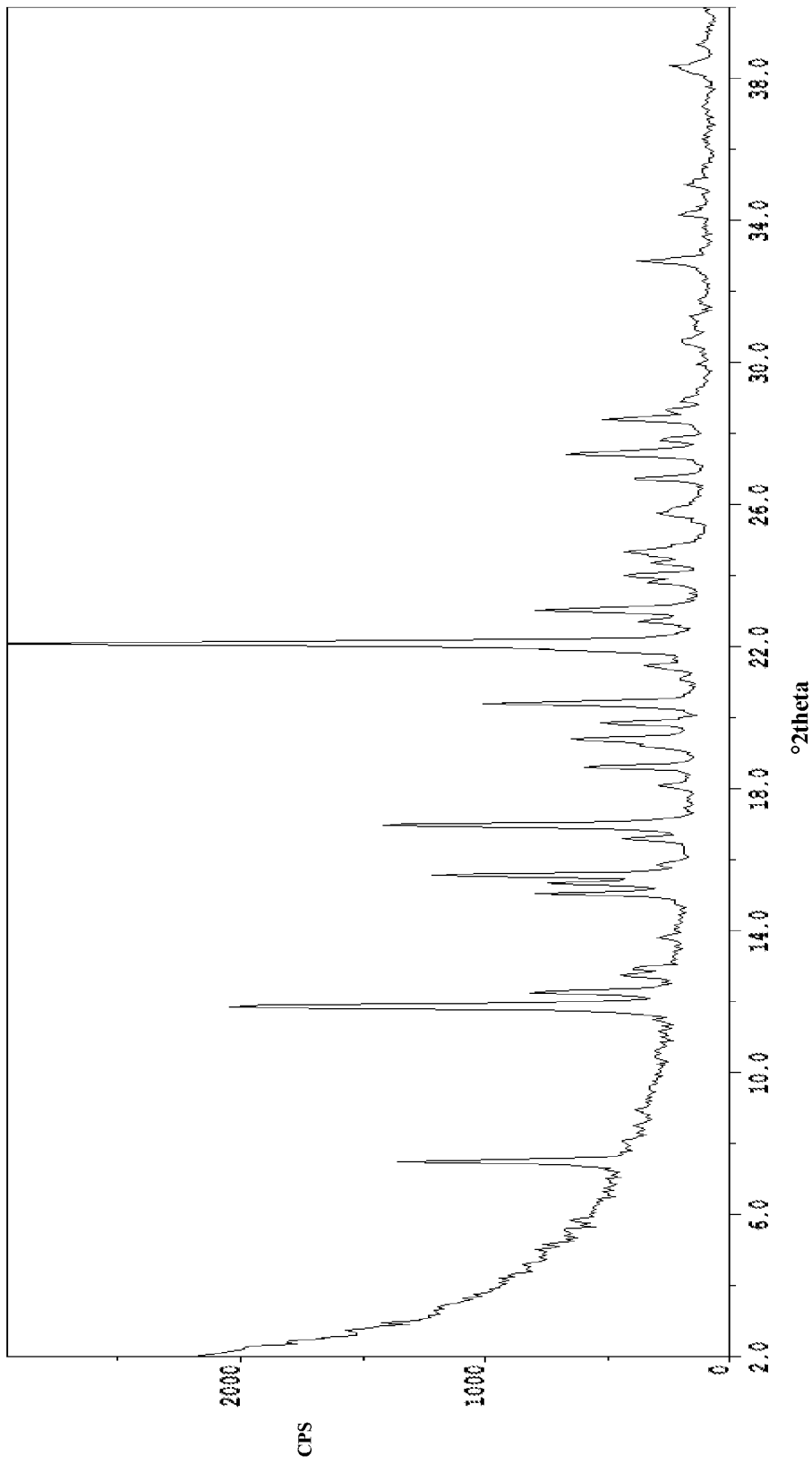
FIG. 4 shows a characteristic XRPD of Mitapivat Form B1.

The present disclosure includes a crystalline polymorph of Mitapivat, designated Form B1. The crystalline Form B1 of Mitapivat may be characterized by data selected from one or more of the following: an X-ray powder diffraction pattern substantially as depicted in FIG. 4; an X-ray powder diffraction pattern having peaks at 7.5, 11.9, 15.6, 17.0, and 22.1 degrees 2-theta±0.2 degrees 2-theta; and combinations of these data.

Crystalline Form B1 of Mitapivat may be further characterized by an X-ray powder diffraction pattern having peaks at 7.5, 11.9, 15.6, 17.0, and 22.1 degrees 2-theta±0.2 degrees 2-theta, and also having any one, two, three, four or five additional peaks selected from 12.3, 15.3, 18.6, 19.4, and 23.0 degrees 2-theta±0.2 degrees 2-theta.

Figure 13:
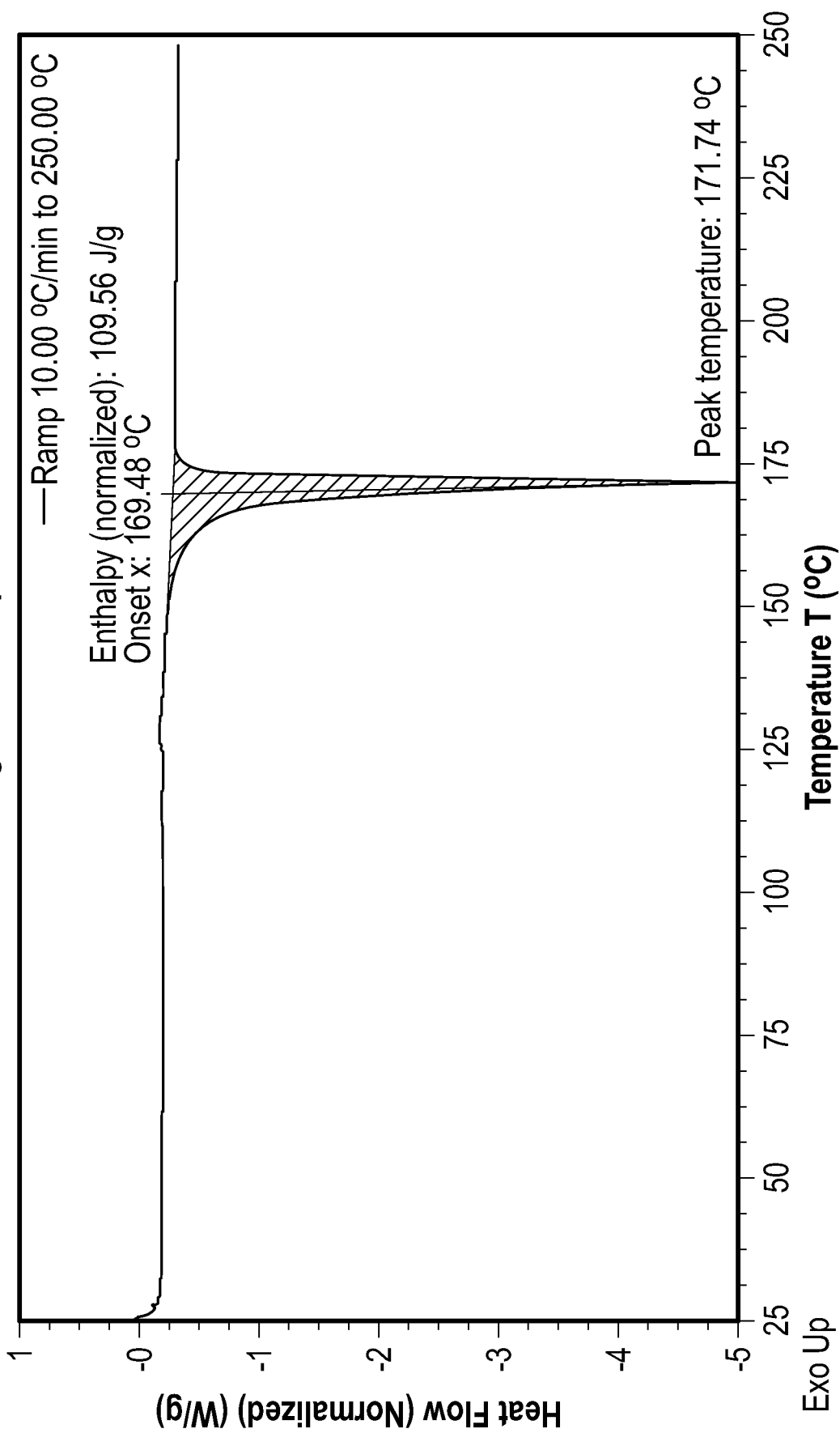
FIG. 13 shows a characteristic DSC thermogram of Mitapivat Form B1.
Figure 14:
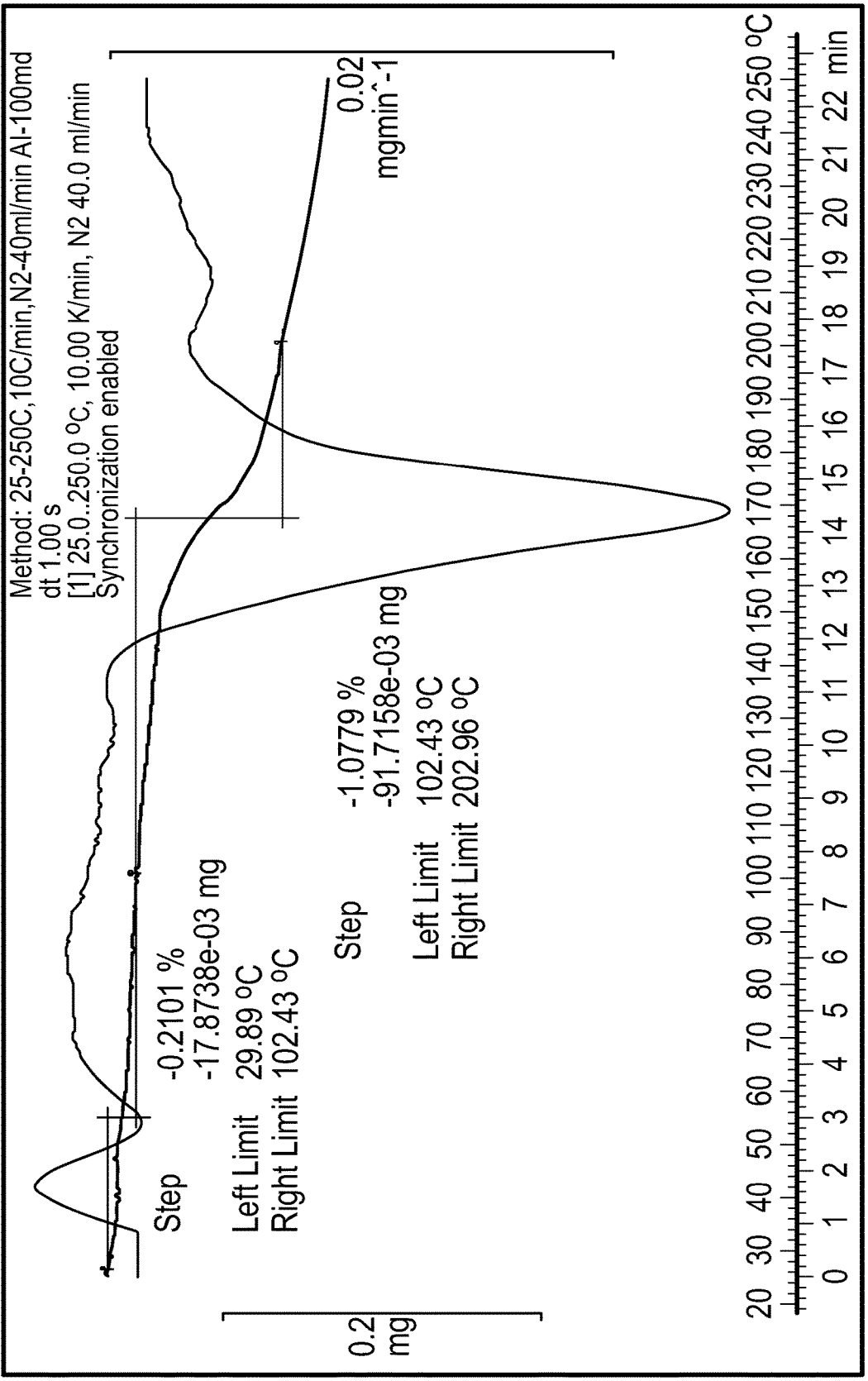
FIG. 14 shows a characteristic TGA thermogram of Mitapivat Form B1.

Crystalline Form B1 of Mitapivat may alternatively or additionally be characterized by data selected from one or more of the following: a DSC thermogram as depicted in FIG. 13; a TGA thermogram as depicted in FIG. 14. Crystalline Form B1 shows a melting endothermic peak at about 171.7° C. according to DSC thermogram. Further, crystalline Form B1 shows weight loss of less than 1.0% of the weight of the sample in a TGA thermogram upon heating up to 250° C. Preferably, Form B1 shows weight loss of less than 1.0% of the weight of the sample in a TGA thermogram. Form B1 shows weight loss of about 0.2% of the weight of the sample in a TGA thermogram.

In one embodiment of the present disclosure, crystalline Form B1 of Mitapivat is isolated.

Crystalline Form B1 of Mitapivat may be anhydrous, hydrate or solvate form. Crystalline Form B1 may be anhydrous.

Crystalline Form B1 of Mitapivat may be characterized by each of the above characteristics alone or by all possible combinations, e.g., an XRPD pattern having peaks at 7.5, 11.9, 15.6, 17.0, and 22.1 degrees 2-theta±0.2 degrees 2-theta; an XRPD pattern as depicted in FIG. 4, and combinations thereof.

The present disclosure encompasses crystalline Mitapivat hemisulfate:ascorbic acid. Crystalline Mitapivat hemisulfate:ascorbic acid may be a co-crystal of Mitapivat hemisulfate and ascorbic acid.

Figure 5:
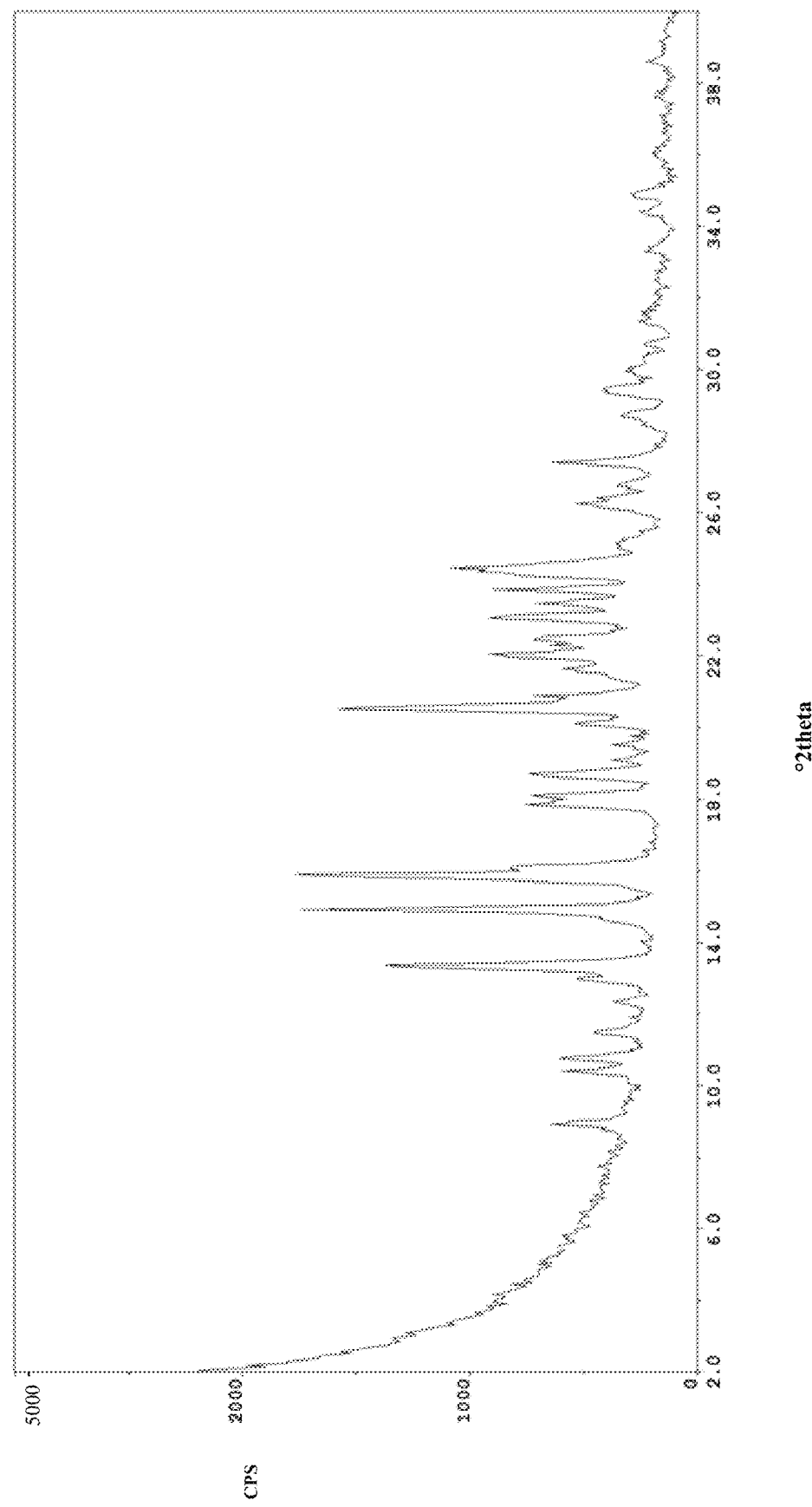
FIG. 5 shows a characteristic XRPD of Mitapivat hemisulfate:ascorbic acid ACC1.

The disclosure further encompasses a crystalline form of Mitapivat hemisulfate and ascorbic acid, designated Form ACC1. Crystalline Form ACC1 of Mitapivat hemisulfate:ascorbic acid may be characterized by data selected from one or more of the following: an X-ray powder diffraction pattern substantially as depicted in FIG. 5; an X-ray powder diffraction pattern having peaks at 8.9, 13.3, 14.9, 15.9, and 20.5 degrees 2-theta±0.2 degrees 2-theta; and combinations of these data.

Crystalline Form ACC1 of Mitapivat hemisulfate:ascorbic acid may be further characterized by an X-ray powder diffraction pattern having peaks at 8.9, 13.3, 14.9, 15.9, and 20.5 degrees 2-theta±0.2 degrees 2-theta, and also having any one, two, three, four or five additional peaks selected from 10.4, 10.7, 18.1, 18.7, and 23.1 degrees 2-theta±0.2 degrees 2-theta.

Figure 15:
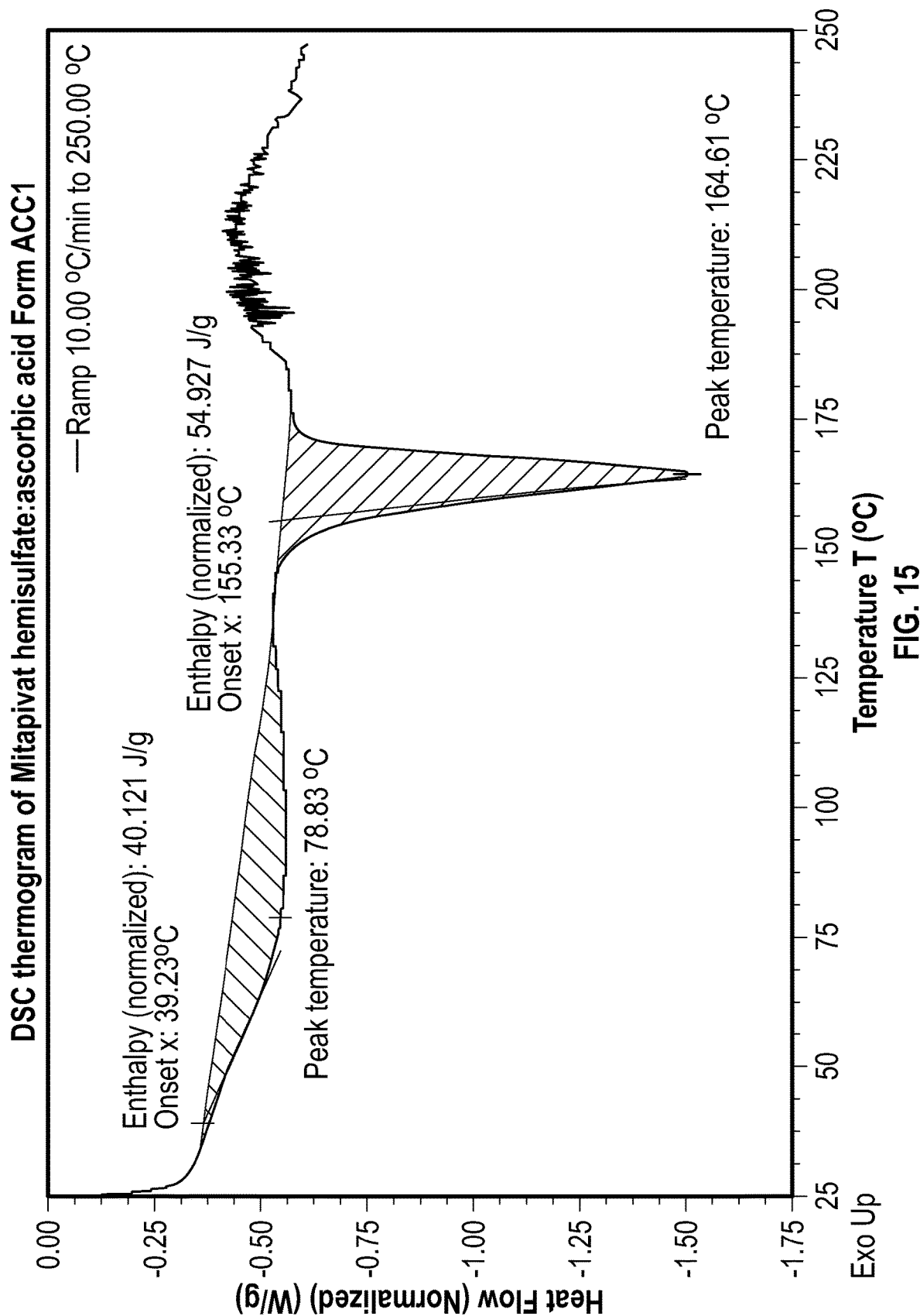
FIG. 15 shows a characteristic DSC thermogram of Mitapivat hemisulfate:ascorbic acid ACC1.
Figure 16:
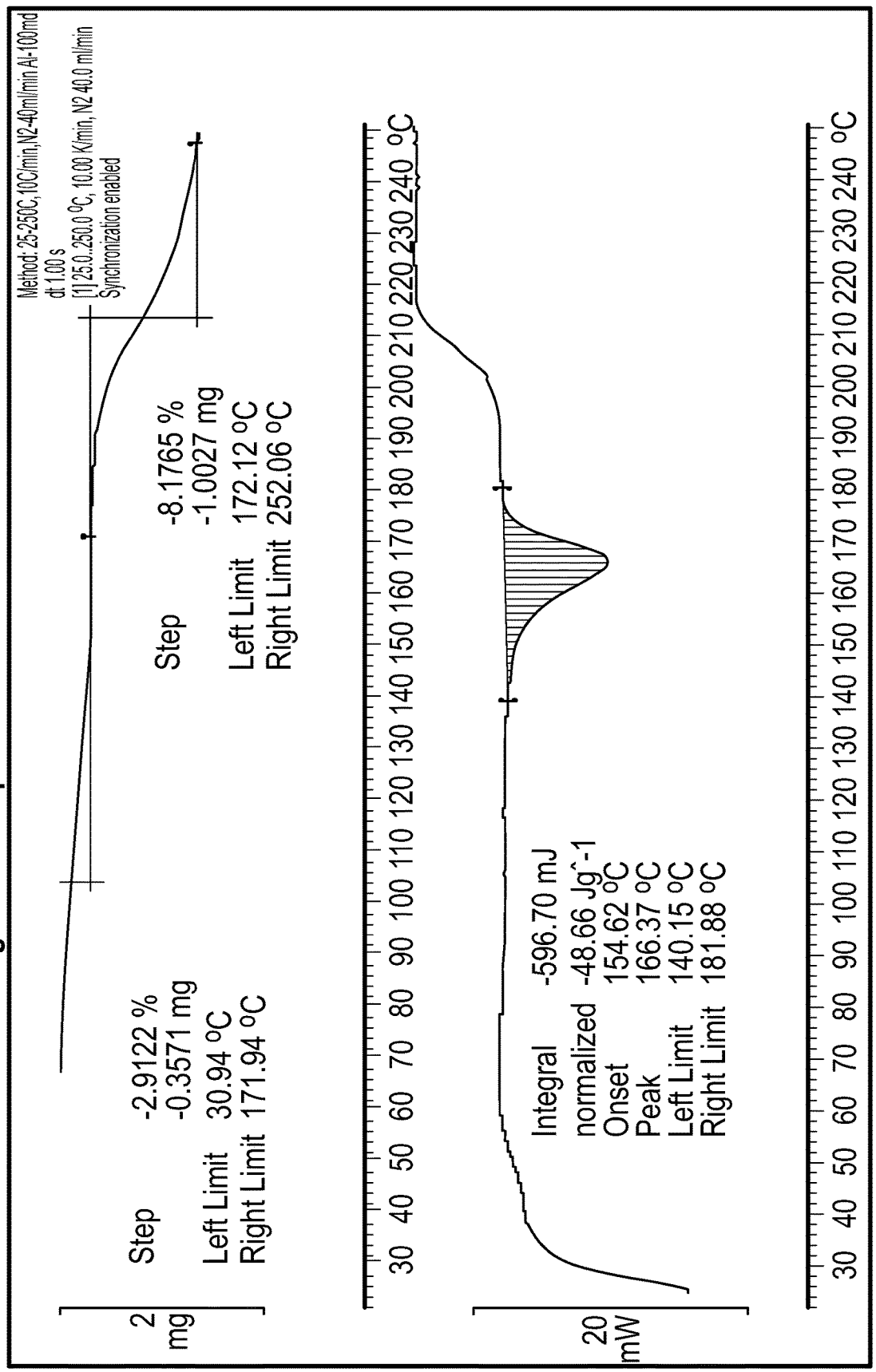
FIG. 16 shows a characteristic TGA/DSC thermogram of Mitapivat hemi sulfate:ascorbic acid ACC1.
Figure 17:
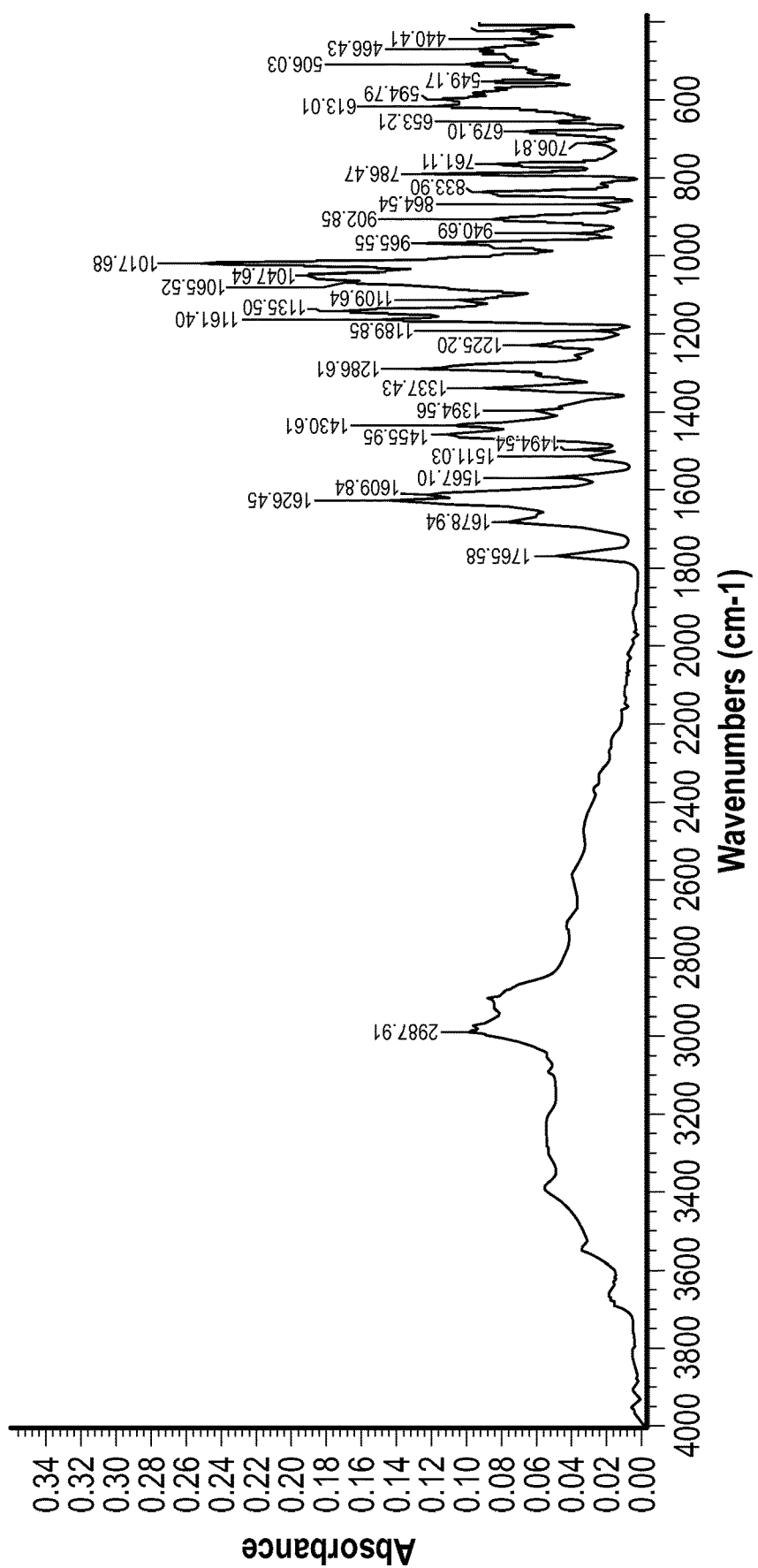
FIG. 17 shows a characteristic FTIR spectrum of Mitapivat hemisulfate:ascorbic acid ACC1.

Crystalline Form ACC1 of Mitapivat hemisulfate:ascorbic acid may alternatively or additionally be characterized by data selected from one or more of the following: a DSC thermogram as depicted in FIG. 15; a TGA/DSC thermogram as depicted in FIG. 16; a FTIR as depicted in FIG. 17. Crystalline Form ACC1 of Mitapivat hemisulfate:ascorbic acid shows a melting endothermic peak at about 164.6° C. according to DSC thermogram. Further, crystalline Form ACC1 of Mitapivat hemisulfate:ascorbic acid shows characteristic FTIR peaks at 1765 cm$^{-1}$ and 1680 cm$^{-1}$±2 cm$^{-1}$.

In embodiments of the present disclosure, crystalline Form ACC1 of Mitapivat hemisulfate:ascorbic acid is isolated.

Crystalline Form ACC1 of Mitapivat hemisulfate:ascorbic acid may be an anhydrous form. Crystalline Form ACC1 of Mitapivat hemisulfate:ascorbic acid may be a hydrate.

Crystalline Form ACC1 of Mitapivat hemisulfate:ascorbic acid may be characterized by each of the above characteristics alone or by all possible combinations, e.g., an XRPD pattern having peaks at 8.9, 13.3, 14.9, 15.9, and 20.5 degrees 2-theta±0.2 degrees 2-theta; an XRPD pattern as depicted in FIG. 5; and combinations thereof.

Crystalline Form ACC1 of Mitapivat hemisulfate:ascorbic acid is polymorphically and chemically stable under regular (60% RH at RT) and accelerated (75% RH at 40° C.) conditions for at least one month. Further, crystalline Form ACC1 of Mitapivat hemisulfate:ascorbic acid is stable under stress conditions like heating, grinding and high pressure. Crystalline Form ACC1 of Mitapivat hemisulfate:ascorbic acid is non-hygroscopic. Crystalline Form ACC1 of Mitapivat hemisulfate:ascorbic acid shows an improved solubility at different pH's compared to Mitapivat hemisulfate.

The present disclosure further encompasses crystalline Mitapivat hemisulfate:adipic acid. Crystalline Mitapivat hemisulfate:adipic acid may be a co-crystal of Mitapivat hemisulfate and adipic acid.

Figure 6:
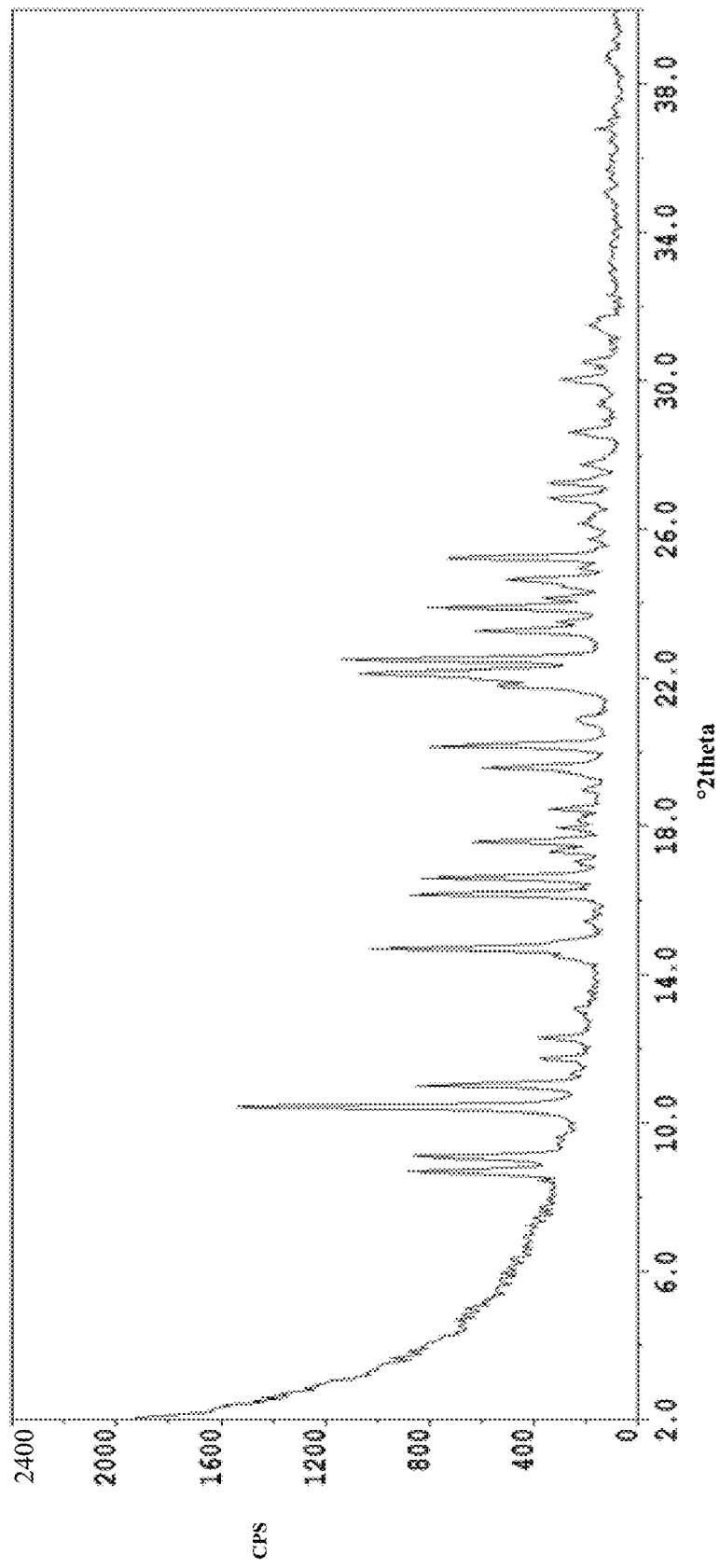
FIG. 6 shows a characteristic XRPD of Mitapivat hemisulfate:adipic acid ACC2.

The disclosure further encompasses a crystalline form of Mitapivat hemisulfate and adipic acid, designated Form ACC2. Crystalline Form ACC2 of Mitapivat hemisulfate:adipic acid may be characterized by data selected from one or more of the following: an X-ray powder diffraction pattern substantially as depicted in FIG. 6; an X-ray powder diffraction pattern having peaks at 10.4, 11.0, 14.7, 16.2, and 16.6 degrees 2-theta±0.2 degrees 2-theta; and combinations of these data.

Crystalline Form ACC2 of Mitapivat hemisulfate:adipic acid may be further characterized by an X-ray powder diffraction pattern having peaks at 10.4, 11.0, 14.7, 16.2, and 16.6 degrees 2-theta±0.2 degrees 2-theta, and also having any one, two, three, four or five additional peaks selected from 8.7, 9.1, 17.6, 20.2, and 22.5 degrees 2-theta±0.2 degrees 2-theta.

Figure 18:
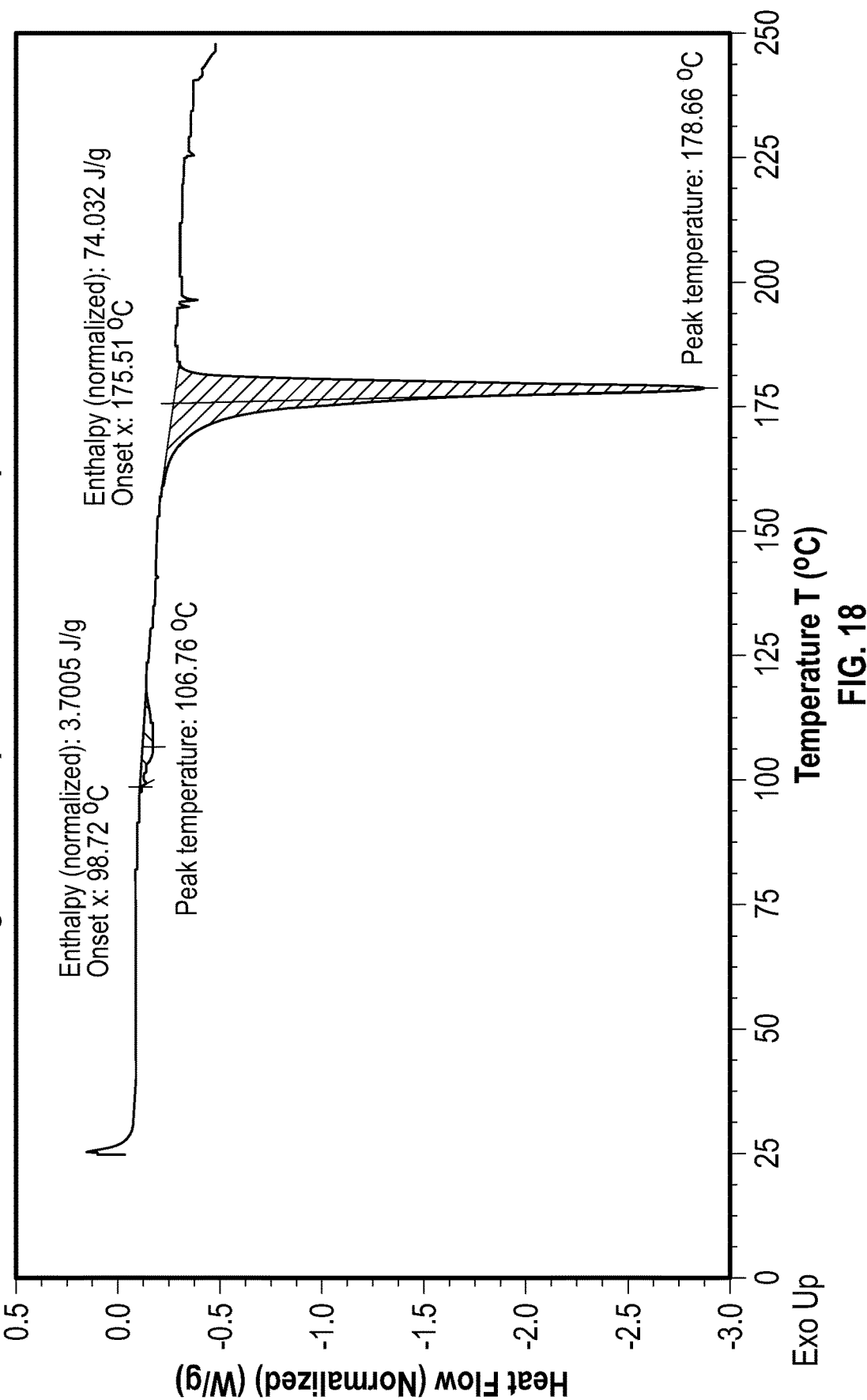
FIG. 18 shows a characteristic DSC thermogram of Mitapivat hemisulfate:adipic acid ACC2.
Figure 19:
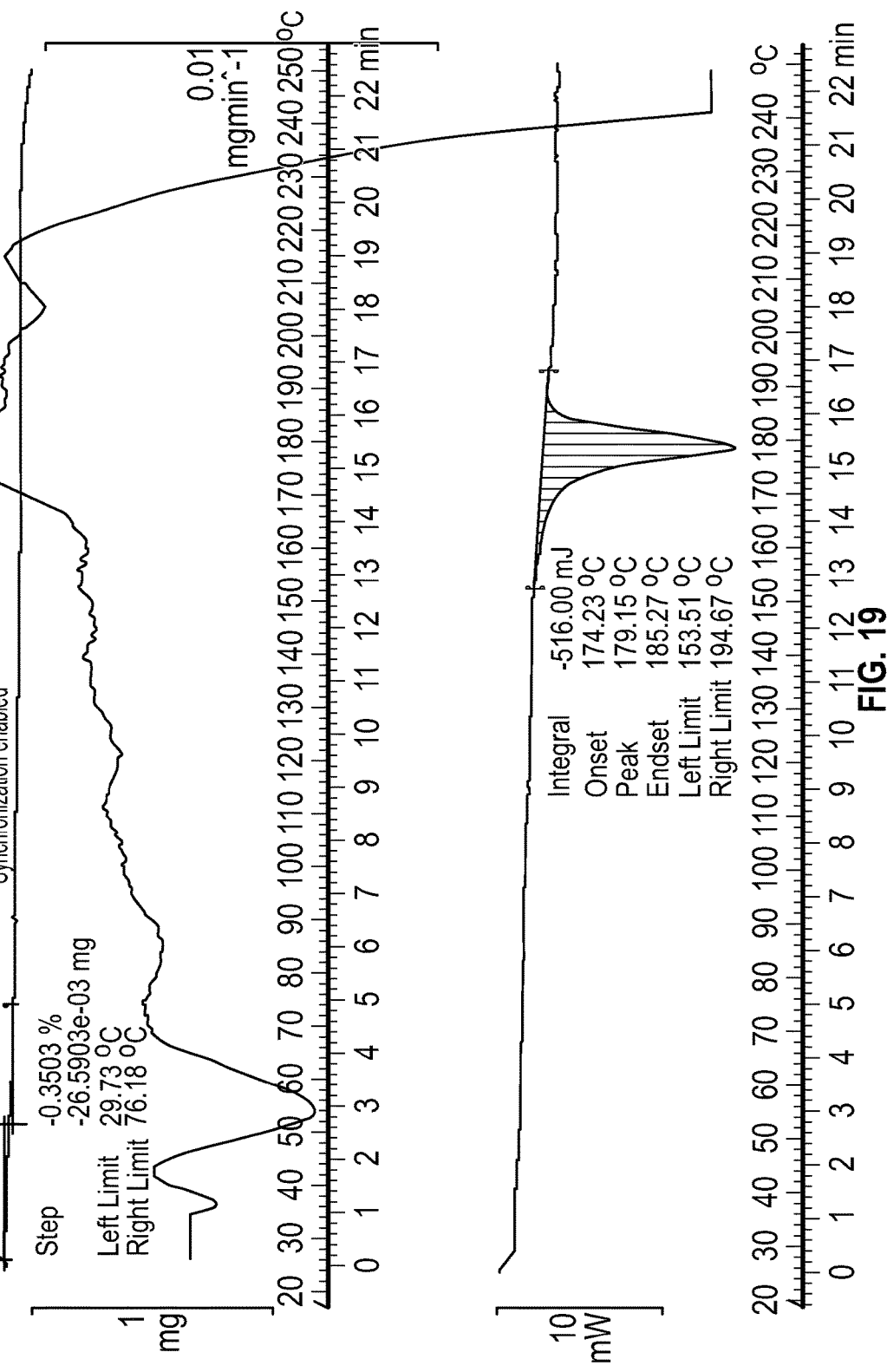
FIG. 19 shows a characteristic TGA/DSC thermogram of Mitapivat hemisulfate:adipic acid ACC2.
Figure 20:
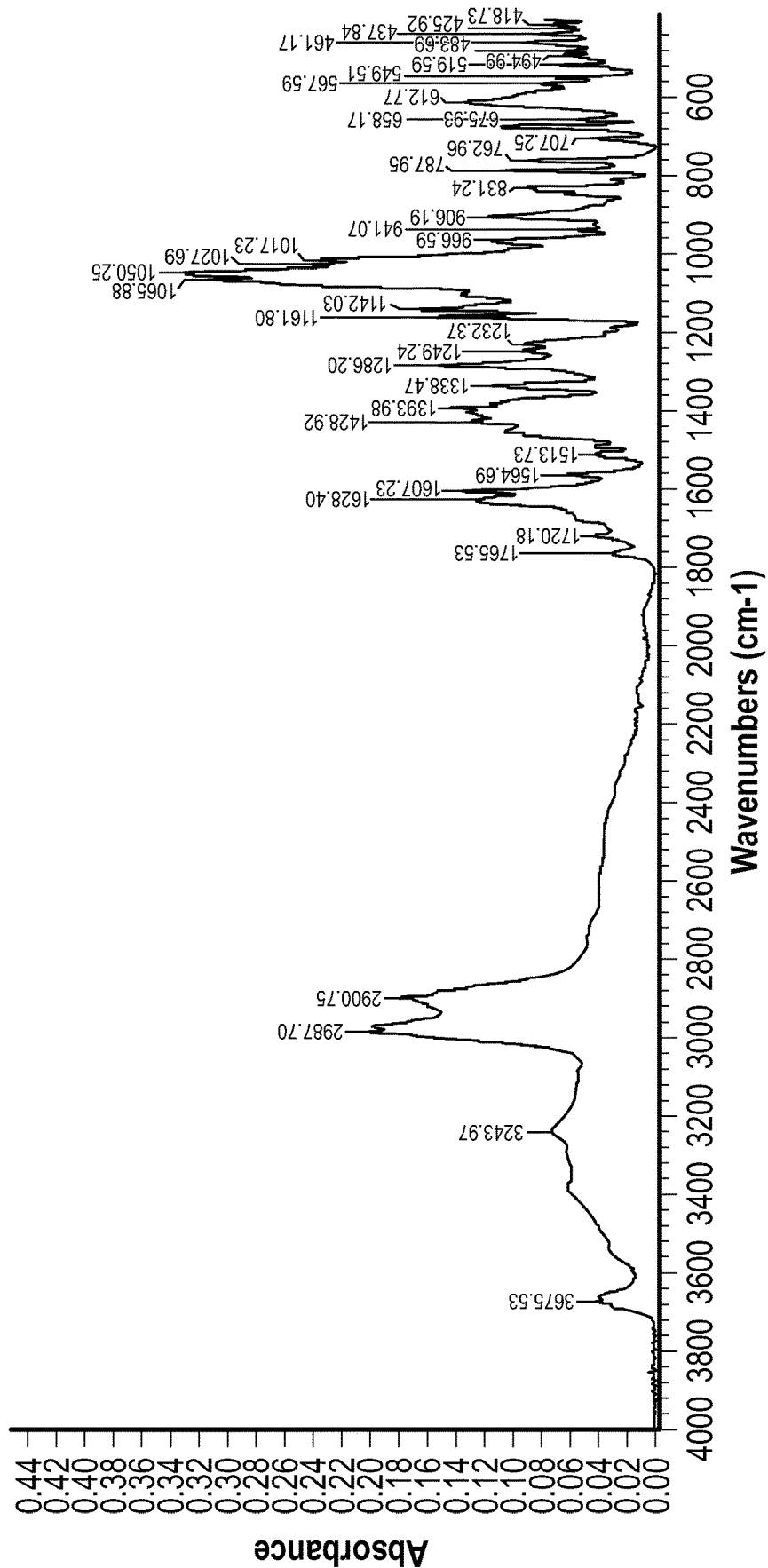
FIG. 20 shows a characteristic FTIR spectrum of Mitapivat hemisulfate:adipic acid ACC2.

Crystalline Form ACC2 of Mitapivat hemisulfate:adipic acid may alternatively or additionally be characterized by data selected from one or more of the following: a DSC thermogram as depicted in FIG. 18; a TGA thermogram as depicted in FIG. 19; or a FTIR as depicted in FIG. 20. Crystalline Form ACC2 of Mitapivat hemisulfate:adipic acid shows a melting endothermic peak at about 178.6° C. according to DSC thermogram. Further, crystalline Form ACC2 of Mitapivat hemisulfate:adipic acid shows weight loss of less than 1% of the weight of the sample in a TGA thermogram upon heating up to 250° C. Preferably, Form ACC2 of Mitapivat hemisulfate:adipic acid shows weight loss of less than 0.5% of the weight of the sample in a TGA thermogram. Form ACC2 of Mitapivat hemisulfate:adipic acid shows weight loss of about 0.3% of the weight of the sample in a TGA thermogram. Further, crystalline Form ACC2 of Mitapivat hemisulfate:adipic acid shows characteristic FTIR peaks at 1721 cm$^{-1}$ and 1638 cm$^{-1}$±2 cm$^{-1}$.

In embodiments of the present disclosure, crystalline Form ACC2 of Mitapivat hemisulfate:adipic acid is isolated.

Crystalline Form ACC2 of Mitapivat hemisulfate:adipic acid may be an anhydrous form. Crystalline Form ACC2 of Mitapivat hemisulfate:adipic acid may be a hydrate.

Crystalline Form ACC2 of Mitapivat hemisulfate:adipic acid may be characterized by each of the above characteristics alone or by all possible combinations, e.g., an XRPD pattern having peaks at 10.4, 11.0, 14.7, 16.2, and 16.6 degrees 2-theta±0.2 degrees 2-theta; an XRPD pattern as depicted in FIG. 6; and combinations thereof.

Crystalline Form ACC2 of Mitapivat hemisulfate:adipic acid is polymorphically and chemically stable under regular (60% RH at RT) and accelerated (75% RH at 40° C.) conditions for at least one month. Further, crystalline Form ACC2 of Mitapivat hemisulfate:adipic acid is stable under stress conditions like heating, grinding and high pressure. Crystalline Form ACC2 of Mitapivat hemisulfate:adipic acid is non-hygroscopic. Crystalline Form ACC2 of Mitapivat hemisulfate:adipic acid shows an improved solubility at different pH's compared to Mitapivat hemisulfate.

Figure 7:
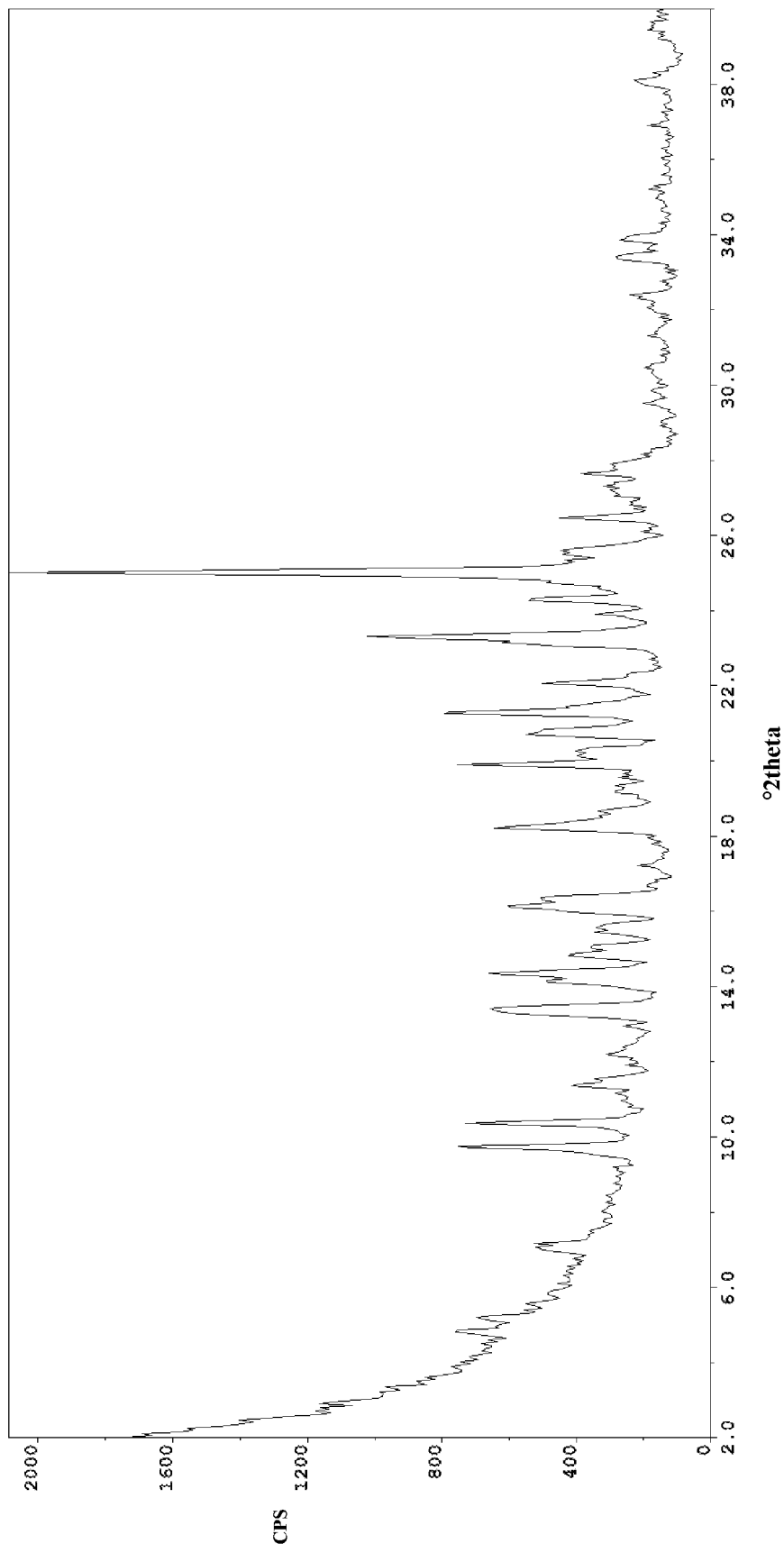
FIG. 7 shows a characteristic XRPD of Mitapivat HCl Form I.

The present disclosure includes a crystalline polymorph of Mitapivat HCl, designated Form I. The crystalline Form I of Mitapivat HCl may be characterized by data selected from one or more of the following: an X-ray powder diffraction pattern substantially as depicted in FIG. 7; an X-ray powder diffraction pattern having peaks at 9.7, 10.3, 13.4, 14.4, and 25.1 degrees 2-theta±0.2 degrees 2-theta; and combinations of these data.

Crystalline Form I of Mitapivat HCl may be further characterized by an X-ray powder diffraction pattern having peaks at 9.7, 10.3, 13.4, 14.4, and 25.1 degrees 2-theta±0.2 degrees 2-theta, and also having any one, two, three, four or five additional peaks selected from 18.2, 19.9, 21.3, 22.1, and 23.3 degrees 2-theta±0.2 degrees 2-theta.

Figure 21:
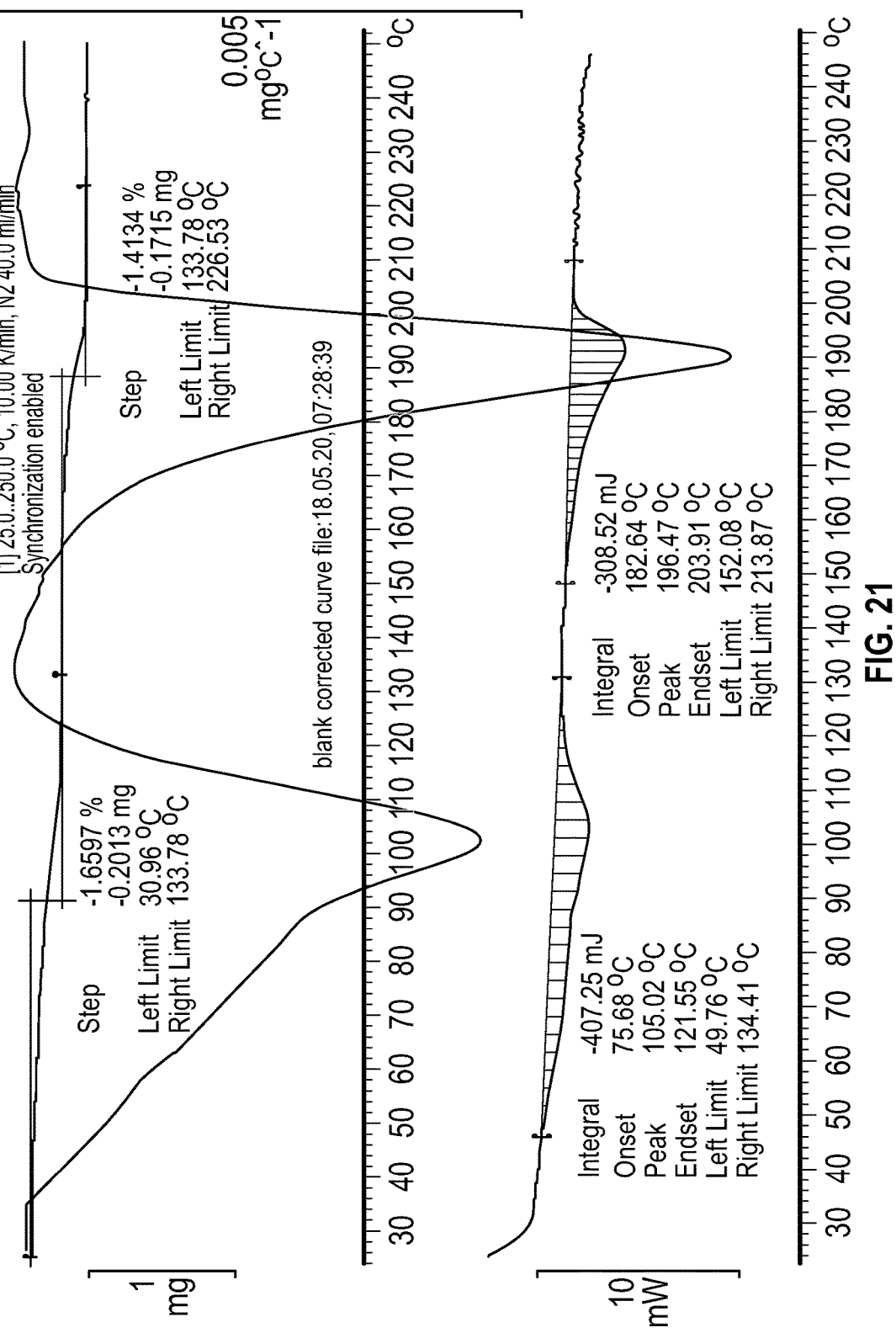
FIG. 21 shows a characteristic TGA/DSC thermogram of Mitapivat HCl Form I.
Figure 22:
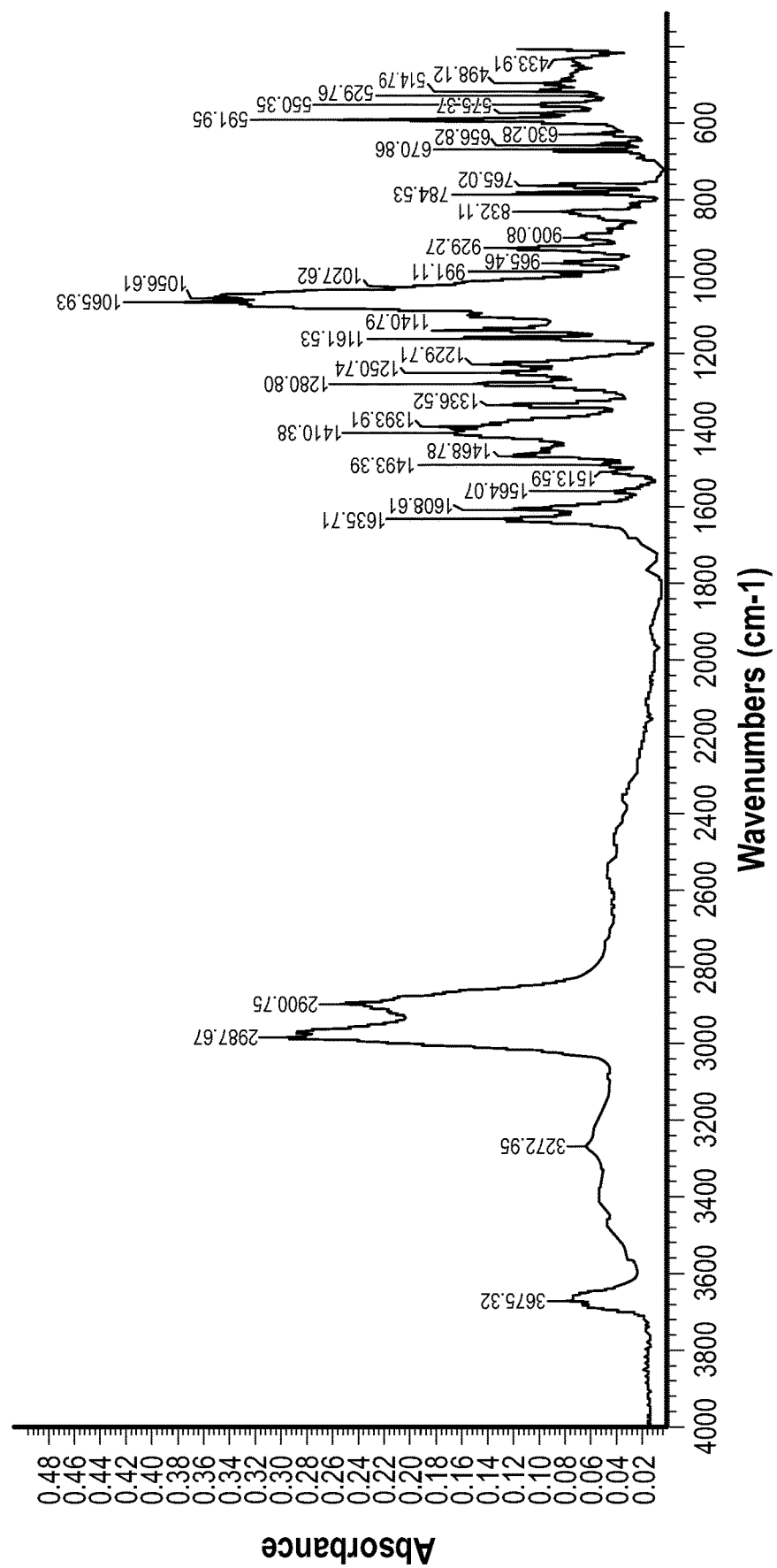
FIG. 22 shows a characteristic FTIR spectrum of Mitapivat HCl Form I.

Crystalline Form I of Mitapivat HCl may alternatively or additionally be characterized by data selected from one or more of the following: a TGA/DSC thermogram as depicted in FIG. 21; or by FTIR spectrum as depicted in FIG. 22.

In one embodiment of the present disclosure, crystalline Form I of Mitapivat HCl is isolated.

Crystalline Form I of Mitapivat HCl may be anhydrous, hydrate or solvate form.

Crystalline Form I of Mitapivat HCl may be characterized by each of the above characteristics alone or by all possible combinations, e.g., an XRPD pattern having peaks at 9.7, 10.3, 13.4, 14.4, and 25.1 degrees 2-theta±0.2 degrees 2-theta; an XRPD pattern as depicted in FIG. 7, and combinations thereof.

Crystalline Form I of Mitapivat HCl is stable under regular (60% RH at RT) and accelerated (75% RH at 40° C.) conditions for at least one month. Further, crystalline Form I of Mitapivat HCl is stable under stress conditions like heating, grinding and high pressure. Crystalline Form I of Mitapivat HCl is non-hygroscopic.

Figure 8:
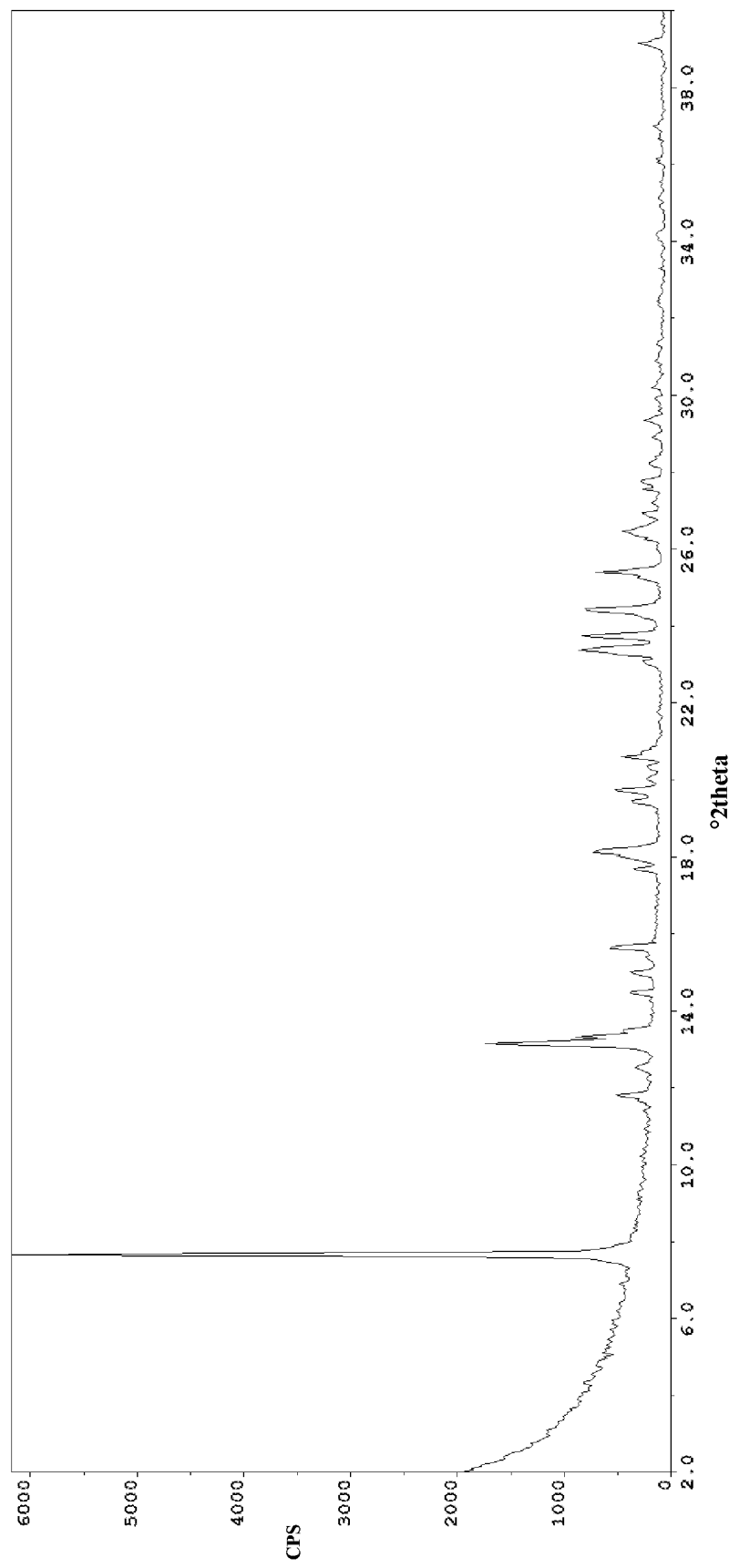
FIG. 8 shows a characteristic XRPD of Mitapivat HCl Form II.

The present disclosure includes a crystalline polymorph of Mitapivat HCl, designated Form II. The crystalline Form II of Mitapivat HCl may be characterized by data selected from one or more of the following: an X-ray powder diffraction pattern substantially as depicted in FIG. 8; an X-ray powder diffraction pattern having peaks at 7.6, 11.8, 13.2, 18.1, and 23.8 degrees 2-theta±0.2 degrees 2-theta; and combinations of these data.

Crystalline Form II of Mitapivat HCl may be further characterized by an X-ray powder diffraction pattern having peaks at 7.6, 11.8, 13.2, 18.1, and 23.8 degrees 2-theta±0.2 degrees 2-theta, and also having any one, two, three, four or five additional peaks selected from 14.9, 15.6, 19.7, 23.4, and 24.4 degrees 2-theta±0.2 degrees 2-theta.

In one embodiment of the present disclosure, crystalline Form II of Mitapivat HCl is isolated.

Crystalline Form II of Mitapivat HCl may be anhydrous, hydrate or solvate form.

Crystalline Form II of Mitapivat HCl may be characterized by each of the above characteristics alone or by all possible combinations, e.g., an XRPD pattern having peaks at 7.6, 11.8, 13.2, 18.1, and 23.8 degrees 2-theta±0.2 degrees 2-theta; an XRPD pattern as depicted in FIG. 8, and combinations thereof.

Figure 9:
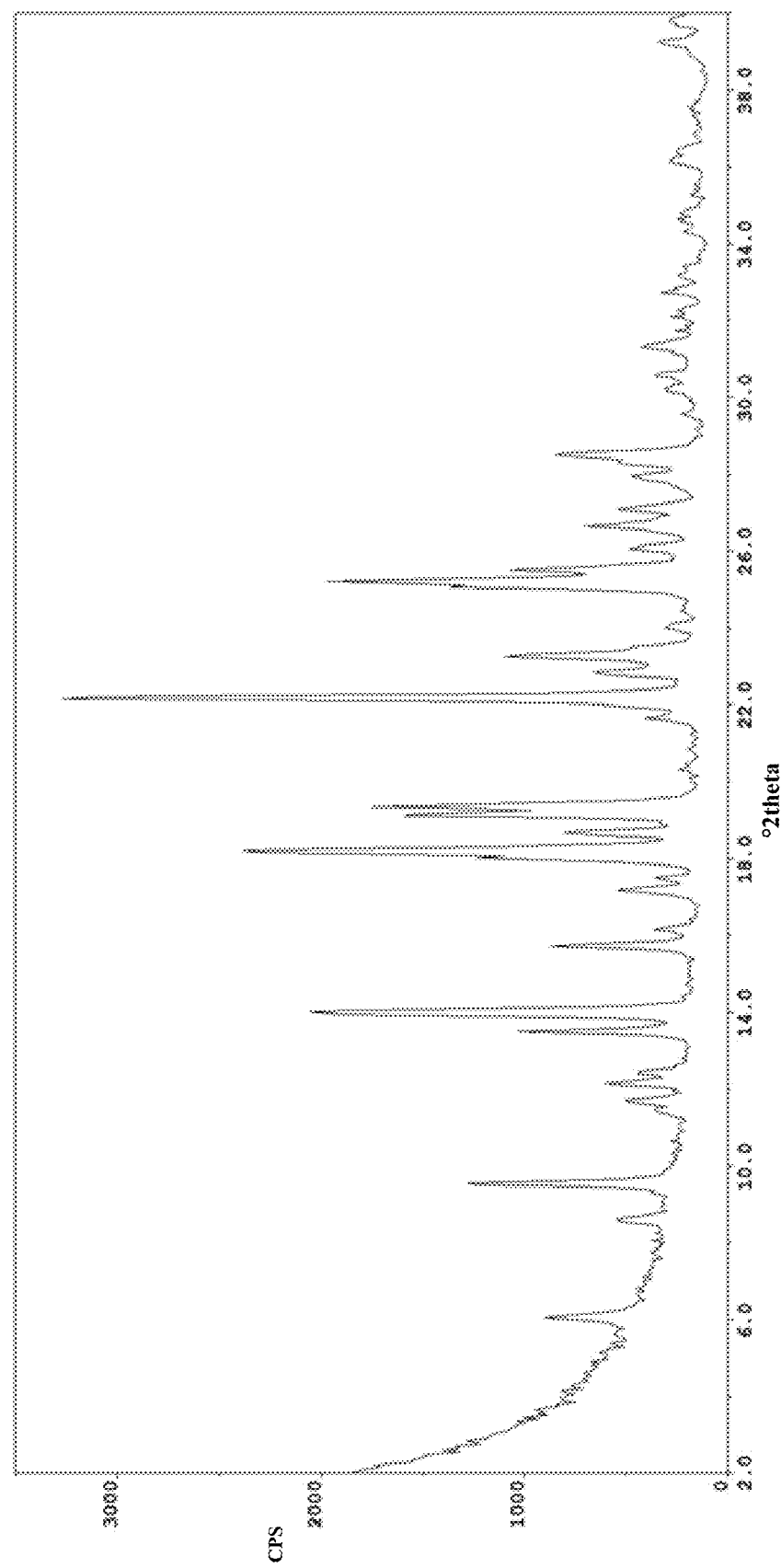
FIG. 9 shows a characteristic XRPD of Mitapivat HCl Form III.

The present disclosure includes a crystalline polymorph of Mitapivat HCl, designated Form III. The crystalline Form III of Mitapivat HCl may be characterized by data selected from one or more of the following: an X-ray powder diffraction pattern substantially as depicted in FIG. 9; an X-ray powder diffraction pattern having peaks at 6.1, 9.5, 13.5, 14.0, and 22.2 degrees 2-theta±0.2 degrees 2-theta; and combinations of these data.

Crystalline Form III of Mitapivat HCl may be further characterized by an X-ray powder diffraction pattern having peaks at 6.1, 9.5, 13.5, 14.0, and 22.2 degrees 2-theta±0.2 degrees 2-theta, and also having any one, two, three, four or five additional peaks selected from 8.6, 15.7, 18.2, 18.7, and 25.2 degrees 2-theta±0.2 degrees 2-theta.

Figure 23:
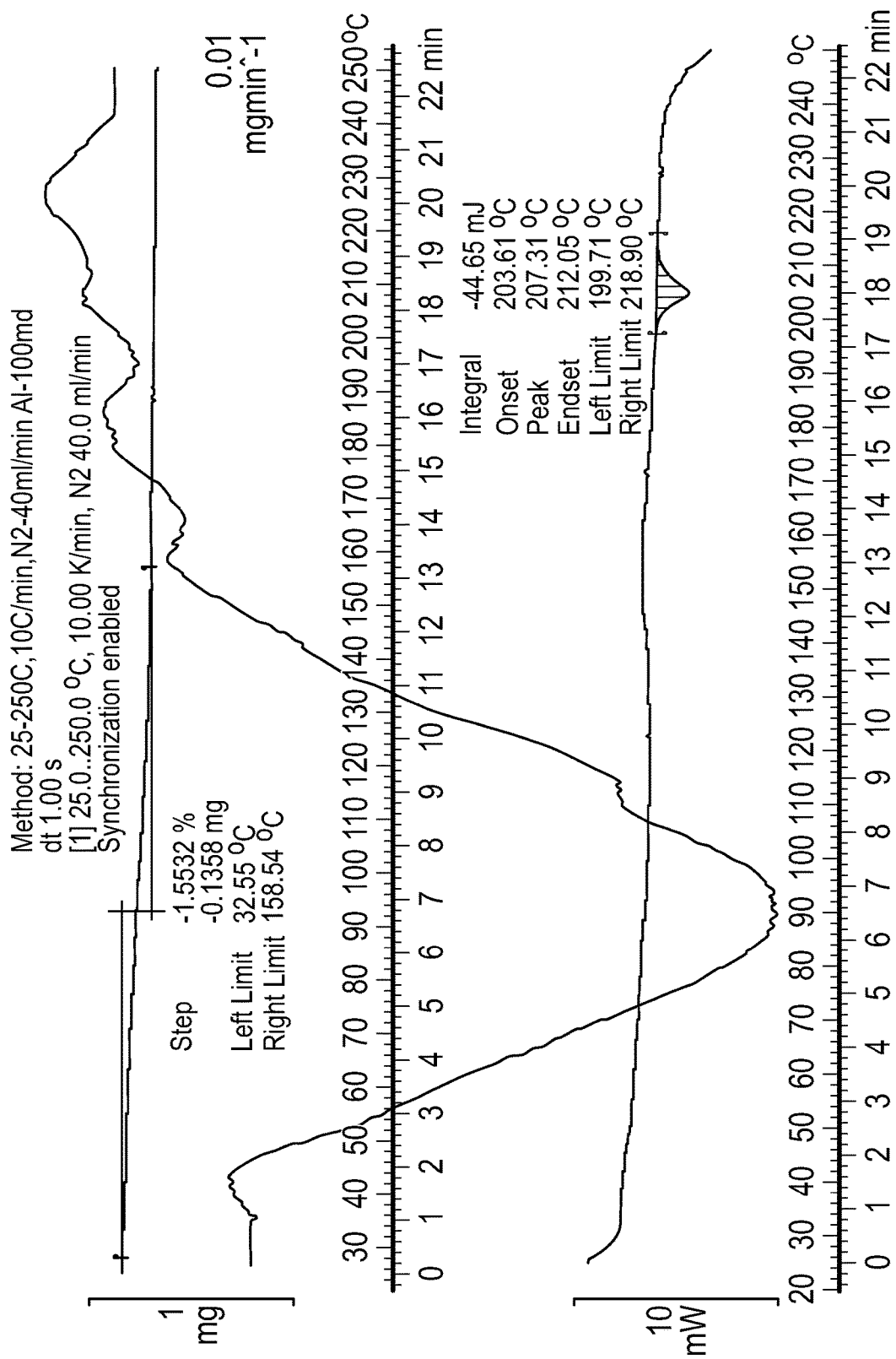
FIG. 23 shows a characteristic TGA/DSC thermogram of Mitapivat HCl Form III.

Crystalline Form III of Mitapivat HCl may alternatively or additionally be characterized by TGA/DSC thermogram as depicted in FIG. 23. Crystalline Form III of Mitapivat HCl shows a melting endothermic peak at about 207.3° C. according to DSC thermogram.

In one embodiment of the present disclosure, crystalline Form III of Mitapivat HCl is isolated.

Crystalline Form III of Mitapivat HCl may be anhydrous, hydrate or solvate form. Crystalline Form III of Mitapivat HCl may be a hemihydrate.

Crystalline Form III of Mitapivat HCl may be characterized by each of the above characteristics alone or by all possible combinations, e.g., an XRPD pattern having peaks at 6.1, 9.5, 13.5, 14.0, and 22.2 degrees 2-theta±0.2 degrees 2-theta; an XRPD pattern as depicted in FIG. 9, and combinations thereof.

Crystalline Form III of Mitapivat HCl is stable up to 80% RH at RT for at least one week. Further, crystalline Form III of Mitapivat HCl is stable under stress conditions like heating, grinding and high pressure. Crystalline Form III of Mitapivat HCl is non-hygroscopic.

Figure 10:
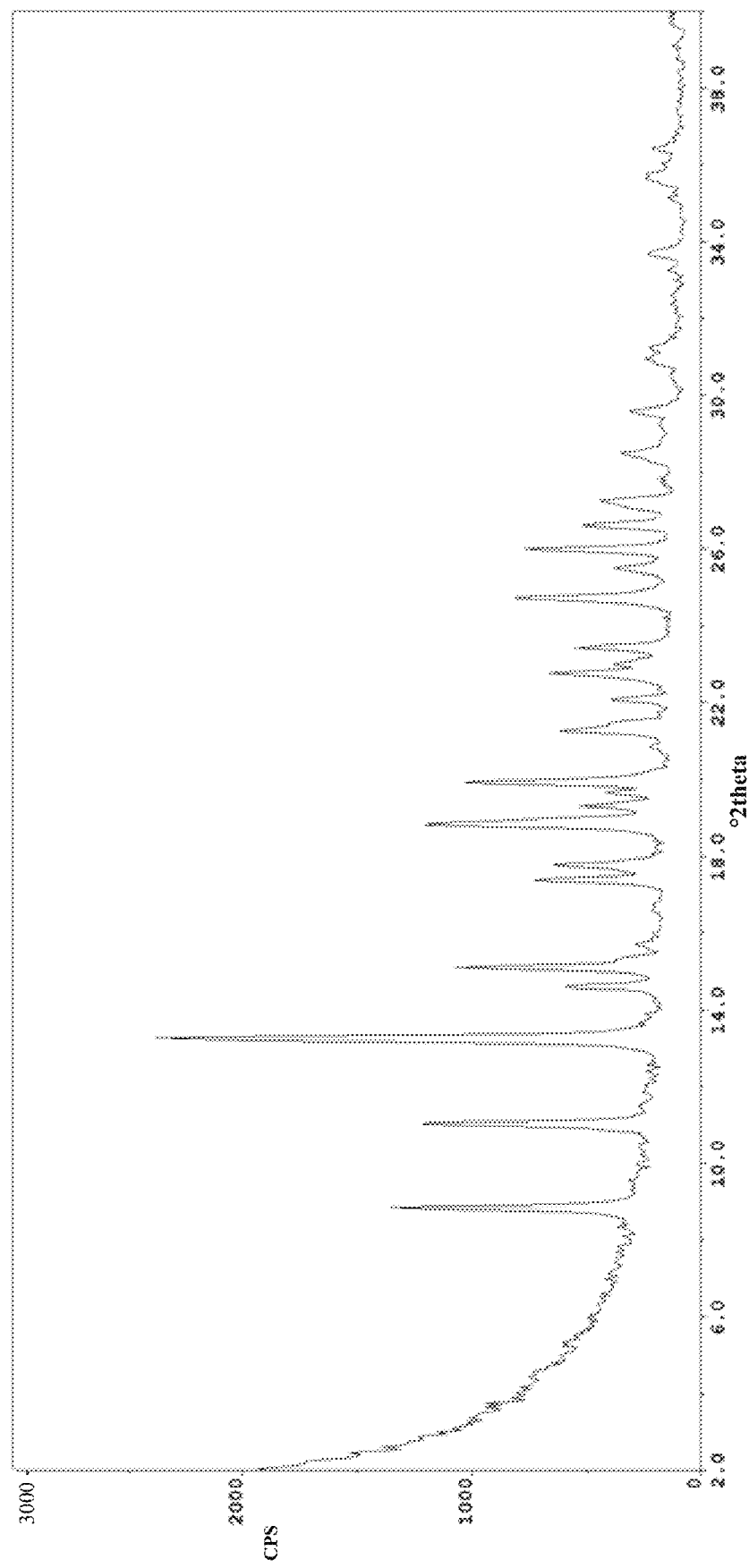
FIG. 10 shows a characteristic XRPD of Mitapivat HCl Form IV.

The present disclosure includes a crystalline polymorph of Mitapivat HCl, designated Form IV. The crystalline Form IV of Mitapivat HCl may be characterized by data selected from one or more of the following: an X-ray powder diffraction pattern substantially as depicted in FIG. 10; an X-ray powder diffraction pattern having peaks at 8.9, 11.1, 13.3, 15.1, and 18.8 degrees 2-theta±0.2 degrees 2-theta; and combinations of these data.

Crystalline Form IV of Mitapivat HCl may be further characterized by an X-ray powder diffraction pattern having peaks at 8.9, 11.1, 13.3, 15.1, and 18.8 degrees 2-theta±0.2 degrees 2-theta, and also having any one, two, three, four or five additional peaks selected from 14.6, 17.4, 17.8, 19.9 and 24.7 degrees 2-theta±0.2 degrees 2-theta.

In one embodiment of the present disclosure, crystalline Form IV of Mitapivat HCl is isolated.

Crystalline Form IV of Mitapivat HCl may be anhydrous, hydrate or solvate form.

Crystalline Form IV of Mitapivat HCl may be characterized by each of the above characteristics alone or by all possible combinations, e.g., an XRPD pattern having peaks at 8.9, 11.1, 13.3, 15.1, and 18.8 degrees 2-theta±0.2 degrees 2-theta; an XRPD pattern as depicted in FIG. 10, and combinations thereof.

Figure 11:
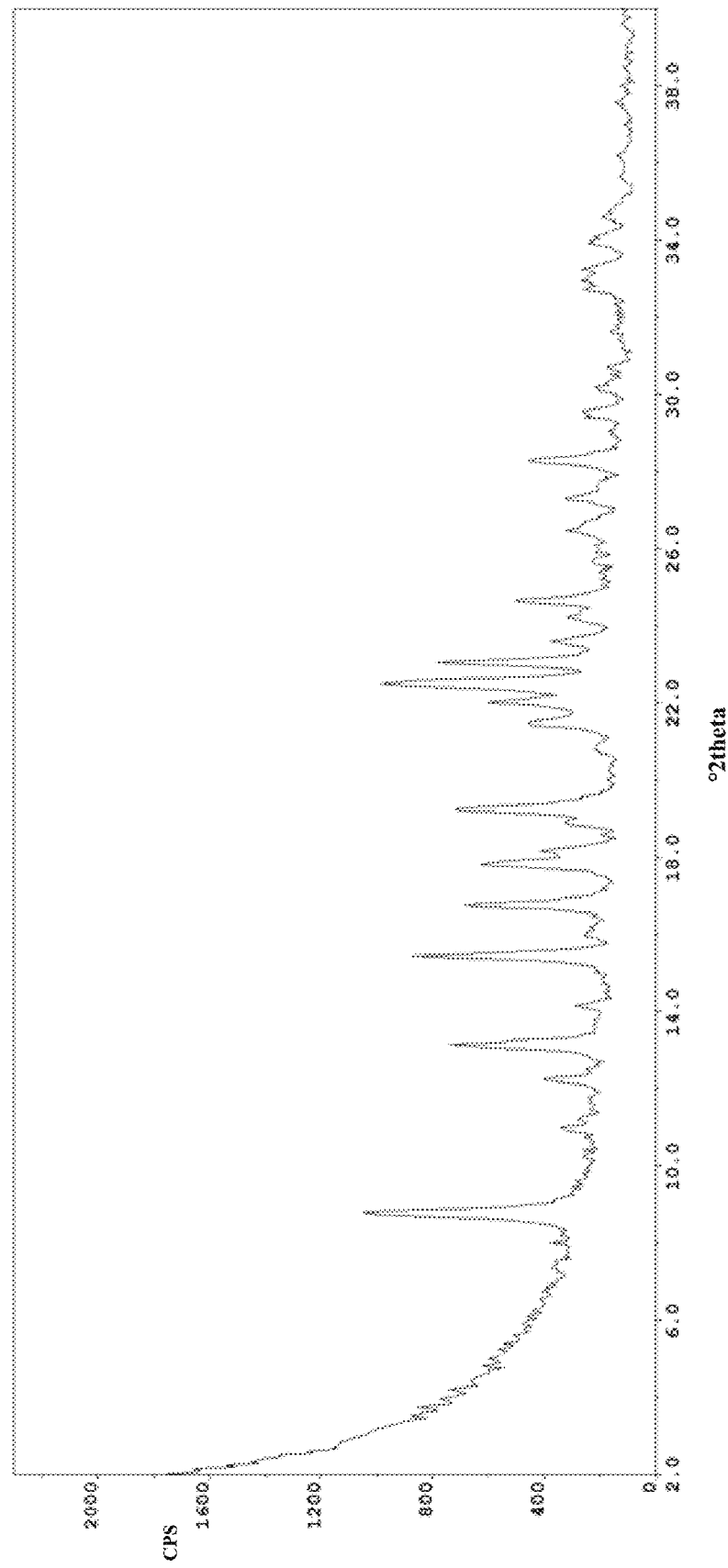
FIG. 11 shows a characteristic XRPD of Mitapivat phosphate Form P1.

The present disclosure includes a crystalline polymorph of Mitapivat phosphate, designated Form P1. The crystalline Form P1 of Mitapivat phosphate may be characterized by data selected from one or more of the following: an X-ray powder diffraction pattern substantially as depicted in FIG. 11; an X-ray powder diffraction pattern having peaks at 8.8, 13.2, 15.5, 16.8, and 19.3 degrees 2-theta±0.2 degrees 2-theta; and combinations of these data. Crystalline Form P1 of Mitapivat phosphate may be further characterized by an X-ray powder diffraction pattern having peaks at 8.8, 13.2, 15.5, 16.8, and 19.3 degrees 2-theta±0.2 degrees 2-theta, and also having any one, two, three, four or five additional peaks selected from 12.3, 17.9, 21.5, 22.5 and 23.1 degrees 2-theta±0.2 degrees 2-theta.

In one embodiment of the present disclosure, crystalline Form P1 of Mitapivat phosphate is isolated.

Crystalline Form P1 of Mitapivat phosphate may be anhydrous, hydrate or solvate form.

Crystalline Form P1 of Mitapivat phosphate may be characterized by each of the above characteristics alone or by all possible combinations, e.g., an XRPD pattern having peaks at 8.8, 13.2, 15.5, 16.8, and 19.3 degrees 2-theta±0.2 degrees 2-theta; an XRPD pattern as depicted in FIG. 11, and combinations thereof.

Crystalline Form P1 of Mitapivat phosphate is stable up to 80% RH at RT for at least one week. Further, crystalline Form P1 of Mitapivat phosphate is stable under grinding. Crystalline Form P1 of Mitapivat phosphate is non-hygroscopic.

The above crystalline polymorphs can be used to prepare other crystalline polymorphs of Mitapivat, Mitapivat salts and their solid state forms or other co-crystals of Mitapivat and their solid states The present disclosure encompasses a process for preparing other solid state forms of Mitapivat, Mitapivat salts and their solid state forms or co-crystals of Mitapivat and their solid state forms. The process includes preparing any one of the solid state forms of Mitapivat, Mitapivat hemisulfate, Mitapivat HCl, Mitapivat phosphate, Mitapivat hemisulfate: ascorbic acid or Mitapivat hemisulfate:adipic acid by the processes of the present disclosure, and converting that solid state form to another solid state form of Mitapivat, another Mitapivat salt or another co-crystal of Mitapivat. The conversion can be done, for example, by a process including basifying any one or a combination of the above described Mitapivat hemisulfate and/or solid state forms thereof, and reacting the obtained Mitapivat base with an appropriate acid, to obtain the corresponding salt.

The present disclosure provides the above described crystalline polymorphs of Mitapivat, Mitapivat hemisulfate, Mitapivat HCl, Mitapivat phosphate, Mitapivat hemisulfate:ascorbic acid or Mitapivat hemisulfate;adipic acid for use in the preparation of pharmaceutical compositions comprising Mitapivat, Mitapivat hemisulfate, Mitapivat HCl, Mitapivat phosphate, Mitapivat hemisulfate:ascorbic acid or Mitapivat hemisulfate;adipic acid and/or crystalline polymorphs thereof.

The present disclosure also encompasses the use of crystalline polymorphs of Mitapivat, Mitapivat hemisulfate, Mitapivat HCl, Mitapivat phosphate, Mitapivat hemisulfate:ascorbic acid or Mitapivat hemisulfate:adipic acid of the present disclosure for the preparation of pharmaceutical compositions comprising Mitapivat, Mitapivat hemisulfate, Mitapivat HCl, Mitapivat phosphate, Mitapivat hemisulfate:ascorbic acid or Mitapivat hemisulfate:adipic acid.

The present disclosure includes processes for preparing the above mentioned pharmaceutical compositions. The processes include combining any one or a combination of the crystalline polymorphs of Mitapivat, Mitapivat hemisulfate, Mitapivat HCl, Mitapivat phosphate, Mitapivat hemisulfate:ascorbic acid or Mitapivat hemisulfate:adipic acid of the present disclosure with at least one pharmaceutically acceptable excipient.

Pharmaceutical combinations or formulations of the present disclosure contain any one or a combination of the solid state forms of Mitapivat, Mitapivat hemisulfate, Mitapivat HCl, Mitapivat phosphate, Mitapivat hemisulfate:ascorbic acid or Mitapivat hemisulfate;adipic acid of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g., Ac-Di-Sol®, Primellose®), colloidal silicon dioxide, croscarmellose sodium, crospovidone (e.g., Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g., Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Mitapivat or Mitapivat hemisulfate and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of Mitapivat, Mitapivat hemisulfate, Mitapivat HCl, Mitapivat phosphate, Mitapivat hemisulfate:ascorbic acid or Mitapivat hemisulfate:adipic acid can be administered. Mitapivat, Mitapivat hemisulfate, Mitapivat HCl, Mitapivat phosphate, Mitapivat hemisulfate:ascorbic acid or Mitapivat hemisulfate:adipic acid may be formulated for administration to a mammal, in embodiments to a human, by injection. Mitapivat, Mitapivat hemisulfate, Mitapivat HCl, Mitapivat phosphate, Mitapivat hemisulfate:ascorbic acid or Mitapivat hemisulfate:adipic acid can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Mitapivat, Mitapivat hemisulfate, Mitapivat HCl, Mitapivat phosphate, Mitapivat hemisulfate:ascorbic acid or Mitapivat hemisulfate:adipic acid and the pharmaceutical compositions and/or formulations of Mitapivat, Mitapivat hemisulfate, Mitapivat HCl, Mitapivat phosphate, Mitapivat hemisulfate:ascorbic acid or Mitapivat hemisulfate:adipic acid of the present disclosure can be used as medicaments, in embodiments in the treatment of Inborn errors of metabolism (IEMs) like Pyruvate kinase deficiencies, thalassemia or sickle cell disease.

The present disclosure also provides methods of treating Inborn errors of metabolism (IEMs) like Pyruvate kinase deficiencies, thalassemia or sickle cell disease by administering a therapeutically effective amount of any one or a combination of the crystalline polymorphs of Mitapivat, Mitapivat hemisulfate, Mitapivat HCl, Mitapivat phosphate, Mitapivat hemisulfate:ascorbic acid or Mitapivat hemisulfate:adipic acid of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("XRPD") Method

XRPD analysis was performed on ARL (SCINTAG) powder X-Ray diffractometer model X'TRA equipped with a solid state detector. Copper radiation of 1.5418 Å was used. Scanning parameters: range: 2-40 degrees two-theta; scan mode: continuous scan; step size: 0.05°, and a rate of 3 deg/min.

TGA Analysis—Mettler Toledo TGA/DSC.
    Scanning parameters:
    Heating between 25-250° C.
    Heating rate: 10° C./min.
    Purging with 40 ml/min N2 flow.
    Sample weight: 7-15 mg.
    Crucible: 150 μL alumina Crucible with standard aluminum lid.
    DSC Analysis—TA Instrument Discovery DSC
    Scanning parameters:
    Heating between 25° C.-250° C., heating rate: 10° C./min.
    Sample weight: 3-8 mg.
    Crucible: T zero Aluminum Pan
    Crucible lid: T zero Aluminum Lid
    Purging with 40 ml/min N2 flow.

FTIR—Thermo Scientific, Nicolet iS5, iD7 ATR
    Measuring parameters:
    Range: 4000-400 cm$^{-1}$ No. of scans: 16
Resolution: 4 cm$^{-1}$

EXAMPLES

Preparation of Starting Materials

Mitapivat can be prepared according to methods known in the literature, for example International Publication No. WO 2011/002817. Mitapivat hemisulfate can be prepared according to methods known from the literature, for example International Publication No. WO2019104134.

Example 1

Preparation of Mitapivat Hemisulfate Form M1

Benzyl alcohol (1.5 ml, 5V) was added to Mitapivat hemisulfate salt (300 mg, 0.28 mmol) to obtain a slurry. The slurry was magnetically stirred and heated to 80° C. over a period of 15 minutes to obtain complete dissolution followed by mechanical filtration using filter disk. Next, isobutyl acetate as anti-solvent (3 ml) was added drop-wise to the stirred clear solution at 80° C. and a light precipitation occurred. The solution was cooled to room temperature with stirring and after 5 hour a massive precipitation occurred. The obtained slurry was stirred at room temperature for additional 24 hours. The solid was then filtered by centrifuge to afford a white wet solid and dried in a vacuum oven at 28° C. over a period of 120 hours to afford white solid. The obtained solid was characterized by X-ray powder diffraction as Mitapivat hemisulfate salt crystal form M1 (FIG. 1).

Example 2

Preparation of Mitapivat Hemisulfate Form M5

Cyrene™ (Dihydrolevoglucosenone 1.3 ml, 13V) was added to Mitapivat hemisulfate salt (100 mg, 0.09 mmol) to obtain a slurry. The slurry was magnetically stirred and heated to 80° C. over a period of 30 minutes to obtain complete dissolution followed by mechanical filtration using a filter disk. Next, water as anti-solvent (3.9 ml) was added drop-wise to the stirred clear solution at 80° C. Then the solution was cooled to room temperature and after 2 hours a massive precipitation occurred. The obtained slurry was stirred at room temperature over a period of 24 hours. The solid was then filtered by centrifuge to afford a white wet solid and dried in vacuum oven at 40° C. over a period of 18 hours to afford a white solid. The obtained solid was characterized by X-ray powder diffraction as Mitapivat hemi sulfate salt crystal form M5 (FIG. 2).

Example 3

Preparation of Mitapivat Hemisulfate Form M6

Dimethyl sulfoxide (0.6 ml, 12V) was added to Mitapivat hemisulfate salt (50 mg, 0.05 mmol) to obtain a slurry. The slurry was magnetically stirred and heated to 50° C. over a period of 30 minutes to obtain complete dissolution followed by mechanical filtration using filter disk. Then the solution was cooled to room temperature and after 2 hours a light precipitation occurred. The obtained mixture was stirred at room temperature over a period of 24 hours. The solid was then filtered by centrifuge to afford white solid and was characterized by X-ray powder diffraction as Mitapivat hemisulfate salt crystal form M6 (FIG. 3).

Example 4

Preparation of Mitapivat Hemisulfate Salt Crystal Form M6

Dimethyl sulfoxide (0.7 ml, 15V) was added to Mitapivat hemisulfate salt (50 mg, 0.05 mmol) to obtain a slurry. The slurry was magnetically stirred and heated to 50° C. over a period of 30 minutes to obtain complete dissolution. The solution was mechanically filtered using filter disk. The solution was placed into a 20 ml vial containing 5 ml of isopropyl alcohol and the vial was hermetically sealed. A light precipitation occurred after 2 days at room temperature. The vial was left for additional 6 days at room temperature. The solid was then filtered by centrifuge to afford a white solid which was characterized by X-ray powder diffraction as Mitapivat hemisulfate salt crystal form M6.

Example 5

Preparation of Mitapivat Hemisulfate Salt Crystal Form M6

Dimethyl sulfoxide (7.2 ml, 12V) was added to Mitapivat hemisulfate salt (600 mg, 0.6 mmol) to obtain a slurry. The slurry was magnetically stirred and heated to 50° C. over a period of 30 minutes to obtain complete dissolution. The solution was mechanically filtered using filter disk. The solution was cooled to room temperature and after 10 minutes a precipitation occurred. The obtained precipitant was stirred at room temperature over a period of 16 hours. The solid was then filtered by centrifuge to afford a white wet solid. The solid was dried in a vacuum oven at 45° C. over a period of 18 hours to afford a white solid which was characterized by X-ray powder diffraction as Mitapivat hemisulfate salt crystal form M6.

Example 6

Preparation of Mitapivat Form B1

Acetonitrile (1 ml, 20V) was added to Mitapivat base (50 mg, 0.11 mmol) to obtain a slurry. The slurry was magnetically stirred and heated to 50° C. over a period of 20 minutes to obtain complete dissolution followed by mechanical filtration using filter disk. The obtained clear mother-liquor was evaporated at 25° C./300-35 mbar to give a solid. The obtained solid was characterized by X-ray powder diffraction as Mitapivat base B1 (FIG. 4).

Example 7

Preparation of Mitapivat Form B1

DMAc (5 ml, 10V) was added to Mitapivat base (500 mg, 1.1 mmol) to obtain a slurry. The slurry was magnetically stirred and heated to 70° C. over a period of 60 minutes to obtain complete dissolution followed by mechanical filtration using filter disk. Next, water as an anti-solvent (8.25 ml) was added drop-wise to the stirred clear solution at 70° C. and stirring was continued for additional 2 hours. Then, the solution was cooled to room temperature and stirred for 13 hours for precipitation. The obtained solid was filtered by centrifuge to afford a white wet solid. The solid was dried in a vacuum oven at 40° C. for 18 hours. The obtained solid was characterized by X-ray powder diffraction as Mitapivat base B1.

Example 8

Preparation of Mitapivat Hemisulfate: Ascorbic Acid Form ACC1

Methanol (1.8 ml, 9V) was added to Mitapivat hemisulfate salt (200 mg, 0.18 mmol) to obtain a slurry. The slurry was magnetically stirred and heated to 50° C. over a period of 15 minutes to obtain complete dissolution followed by filtration using filter disk. Next, ascorbic acid (33 mg, 0.18 mmol) was added to the stirred clear solution at 50° C. and stirred at 50° C. over a period of 15 minutes to complete dissolution. Next, acetone as anti-solvent (3.2 ml) was added drop-wise to the stirred clear solution at 50° C. The solution was cooled to room temperature and then stirred at room temperature during 96 hours. The obtained precipitation was then filtered by centrifuge to afford a white wet solid, which was dried in a vacuum oven at 45° C. over a period of 24 hours to afford white solid. The obtained solid was characterized by X-ray powder diffraction as Mitapivat hemisulfate:ascorbic acid crystal Form ACC1 (FIG. 5).

Example 9

Preparation of Mitapivat Hemisulfate: Ascorbic Acid Form ACC1

Methanol (1.8 ml, 9V) was added to Mitapivat hemisulfate salt (200 mg, 0.18 mmol) to obtain a slurry. The slurry was magnetically stirred and heated to 50° C. over a period of 15 minutes to obtain complete dissolution followed by filtration using filter disk. Next, ascorbic acid (33 mg, 0.18 mmol) was added to the stirred clear solution at 50° C. and stirred at 50° C. over a period of 15 minutes to complete dissolution. Methyl ethyl ketone (MEK) as anti-solvent (3.2 ml) was added drop-wise to the stirred clear solution at 50° C. The solution was cooled to room temperature and stirred at room temperature for 18 hours. The obtained precipitation was filtered by centrifuge to afford a white wet solid, which was dried in a vacuum oven at 45° C. over a period of 16 hours to afford white solid. The obtained solid was characterized by X-ray powder diffraction as Mitapivat hemisulfate ascorbic acid crystal form ACC1.

Example 10

Preparation of Mitapivat Hemisulfate: Ascorbic Acid Form ACC1

Methanol (0.4 ml, 5V) was added to Mitapivat hemisulfate salt (100 mg, 0.09 mmol) to obtain a slurry. The slurry was magnetically stirred and heated to 50° C. over a period of 15 minutes to obtain complete dissolution followed by filtration using filter disk. Next, ascorbic acid (33 mg, 0.19 mmol) was added to the stirred clear solution at 50° C. and stirred at 50° C. over a period of 15 minutes to complete dissolution. The solution was cooled to room temperature and then stirred at 4° C. for 3 weeks. The obtained precipitation was filtered by centrifuge to afford a white wet solid, which was dried in a vacuum oven at 45° C. over a period of 4 hours to afford white solid. The obtained solid was characterized by X-ray powder diffraction as Mitapivat hemisulfate ascorbic acid crystal form ACC1.

Example 11

Preparation of Mitapivat Hemisulfate: Ascorbic Acid Form ACC1

Methanol (8 ml, 8V) was added to Mitapivat hemisulfate salt (1 gr, 0.9 mmol) to obtain a slurry. The slurry was magnetically stirred and heated to 50° C. over a period of 15 minutes to obtain complete dissolution followed by filtration using filter disk. Next, ascorbic acid (168 mg, 0.96 mmol) was added to the stirred clear solution at 50° C. and stirred at 50° C. over a period of 15 minutes to complete dissolution. The solution was seeded with Form ACC1 (5% w/w) and Methyl ethyl ketone (MEK) as anti-solvent (16 ml) was added drop-wise to induce precipitation. The obtained slurry was cooled to room temperature and stirred at room temperature for 24 hours. The obtained precipitation was filtered by centrifuge to afford a white wet solid. The solid was dried in a vacuum oven at 45° C. over a period of 16 hours to afford white solid. The obtained solid was characterized by X-ray powder diffraction as Mitapivat hemisulfate:ascorbic acid crystal form ACC1.

Example 12

Preparation of Mitapivat Hemisulfate: Adipic Acid Form ACC2

Methanol (0.8 ml, 4V) was added to Mitapivat hemisulfate salt (200 mg, 0.18 mmol) to obtain a slurry. The slurry was magnetically stirred and heated to 50° C. over a period of 15 minutes to obtain complete dissolution followed by filtration using filter disk. Next, adipic acid (28 mg, 0.19 mmol) was added to the stirred clear solution at 50° C. and stirred at 50° C. over a period of 15 minutes to complete dissolution. Next, Methyl ethyl ketone (MEK) as an anti-solvent (2.4 ml) was added drop-wise to the stirred clear solution at 50° C. The solution was cooled to room temperature and then stirred at room temperature for 20 hours. The obtained precipitation was then filtered by centrifuge to afford a white wet solid and dried in a vacuum oven at 45° C. over a period of 20 hours to afford white solid. The obtained solid was characterized by X-ray powder diffraction as Mitapivat hemisulfate salt:adipic acid crystal form ACC2 (FIG. 6).

Example 13

Preparation of Mitapivat Hemisulfate: Adipic Acid Form ACC2

Methanol (2 ml, 4V) was added to Mitapivat hemisulfate salt (500 mg, 0.45 mmol) to obtain a slurry. The slurry was magnetically stirred and heated to 50° C. over a period of 15 minutes to obtain complete dissolution followed by filtration using filter disk. Next, adipic acid (69 mg, 0.47 mmol) was added to the stirred clear solution at 50° C. and stirred at 50° C. over a period of 15 minutes to complete dissolution. Methyl ethyl ketone (MEK) as an anti-solvent (2.4 ml) was added drop-wise to the stirred clear solution at 50° C. The solution was cooled to room temperature and was seeded with Form ACC2 (5% w/w). The obtained precipitation was stirred at room temperature for 20 hours. The obtained solid was then filtered by centrifuge to afford a white wet solid.

The solid was dried in a vacuum oven at 45° C. over a period of 20 hours to afford white solid. The obtained solid was characterized by X-ray powder diffraction as Mitapivat hemisulfate salt:adipic acid crystal form ACC2.

Example 14

Preparation of Mitapivat HCl Form I

Ethyl acetate (5 ml, 10V) was added to Mitapivat base (500 mg, 1.1 mmol) to obtain a slurry. The slurry was magnetically stirred and 37% HCl aqua solution (0.115 ml, 1.1 eq.) was added. Next, the slurry was stirred at room temperature over a period of 72 hours. The obtained solid was filtered by centrifuge, washed twice with Ethyl acetate (1V) and dried in a vacuum oven at 45° C. for 24 hours. The obtained solid was characterized by X-ray powder diffraction as Mitapivat HCl Form I (FIG. 7).

Example 15

Preparation of Mitapivat HCl Form II

Water (0.65 ml, 13V) was added to Mitapivat HCl salt crystal Form I (50 mg, 0.1 mmol) to obtain a slurry. The slurry was magnetically stirred at room temperature over a period of 20 hours. The solid was then filtered by centrifuge to afford a white wet solid. The obtained solid was characterized by X-ray powder diffraction as Mitapivat HCl Form II (FIG. 8).

Example 16

Procedure for Preparation of Mitapivat HCl Form II

A mixture of water and methanol (5:95) (1.6 ml, 8V) was added to Mitapivat base (200 mg, 0.44 mmol) to obtain a slurry. The slurry was magnetically stirred and heated to 50° C. over a period of 15 minutes and then 37% HCl aqua solution (0.048 ml, 1.1 eq.) was added to the obtained clear solution. Water was added (20 ml, 100V) to the stirred clear solution at 50° C. and was stirred for 30 min. The solution was cooled to 15° C. and an additional portion of water was added (0.8 ml, 4V) and stirred at 15° C. over a period of 16 hours. Next, the solution was cooled to 4° C. and stirred at 4° C. over a period of 62 hours. Then, heptane as an anti-solvent (0.3 ml) was added drop-wise and after 2 hours massive precipitation occurred. The obtained solid was separated by Buchner, washed with 0.8 ml mixture of water and methanol (1:1) and was characterized by X-ray powder diffraction as Mitapivat HCl Form II.

Example 17

Procedure for Preparation of Mitapivat HCl Form III

Mitapivat HCl Form II that was prepared according to Example 16 was dried in a vacuum oven at 45° C. for 24 hours. The obtained solid was characterized by X-ray powder diffraction as Mitapivat HCl Form III.

Example 18

Preparation of Mitapivat HCl Form III

Mitapivat HCl salt crystal Form II was dried in a vacuum oven at 45° C. during 8 hours and the solid was characterized by X-ray powder diffraction as Mitapivat HCl Form III (FIG. 9).

Example 19

Preparation of Mitapivat HCl Form IV

Dioxane (6 ml, 30V) was added to Mitapivat base (200 mg, 0.44 mmol) to obtain a slurry. The slurry was magnetically stirred and heated to 60° C. over a period of 15 minutes to obtain complete dissolution followed by filtration using filter disk. Next, HCl 4M dioxane solution (0.12 ml, 1.1 eq) was added to give a precipitation. The obtained slurry was cooled to room temperature and then stirred at room temperature during 24 hours. The obtained solid was filtered by centrifuge, washed twice with dioxane (1V*2) and dried in a vacuum oven at 45° C. for 24 hours. The obtained solid was characterized by X-ray powder diffraction as Mitapivat HCl Form IV (FIG. 10).

Example 20

Preparation of Mitapivat phosphate Form P1

A mixture of methanol and water (95:5) (6 ml, 8V) was added to Mitapivat base (750 mg, 1.6 mmol) and magnetically stirred at room temperature. Then, 85% phosphoric acid aqua solution (0.34 ml, 3 eq.) was added. The mixture was magnetically stirred and heated to 50° C. to obtain complete dissolution. Next, additional portion of water (0.375 ml, 0.5V) was added and solution held for 10 minutes and then cooled to 25° C. over 1 hour. Then, water (3 ml, 4V) was added and the mixture was magnetically stirred at 25° C. for 20 minutes. The mixture was cooled down to 15° C. over 1 hour and after 1 hour at 15° C. a massive precipitation occurred. The obtained slurry was stirred at 15° C. over 30 minutes and then was filtered by Buchner, washed 4 times with a mixture of methanol and water (1:1) (2V) and dried in a vacuum oven at 45° C. during 18 hours. The obtained solid was characterized by X-ray powder diffraction as Mitapivat phosphate salt crystal form P1 (FIG. 11).

Further aspects and embodiments of the present disclosure are set out in the numbered clauses below:
1. Crystalline Mitapivat hemi sulfate:ascorbic acid.
2. Crystalline Mitapivat hemi sulfate:ascorbic acid, which is a co-crystal.
3. A crystalline product according to Clause 1 or 2, designated Form ACC1, which is characterized by data selected from one or more of the following:
   a. an XRPD pattern having peaks at 8.9, 13.3, 14.9, 15.9, and 20.5 degrees 2-theta±0.2 degrees 2-theta;
   b. an XRPD pattern as depicted in FIG. 1; and
   c. combinations of these data.
4. A crystalline product according to any of Clauses 1, 2, or 3, designated Form ACC1, characterized by the XRPD pattern having peaks at 8.9, 13.3, 14.9, 15.9, and 20.5 degrees 2-theta±0.2 degrees 2-theta, and also having one, two, three or four additional peaks selected from 10.4, 10.7, 18.1, 18.7, and 23.1 degrees two theta±0.2 degrees two theta.

5. A crystalline product according to any of Clauses 1, 2, 3, or 4, designated Form ACC1 which contains: no more than about 20%, no more than about 10%, no more than about 5%, no more than about 2%, no more than about 1% or about 0% of any other crystalline forms of Mitapivat hemi sulfate:ascorbic acid.

6. A crystalline product according to any of Clauses 1, 2, 3, 4, or 5, designated form ACC1, which contains: no more than about 20%, no more than about 10%, no more than about 5%, no more than about 2%, no more than about 1% or about 0% of amorphous Mitapivat hemi sulfate:ascorbic acid.

7. A process for the preparation of a crystalline product according to any of Clauses 1, 2, 3, 4, 5 or 6, designated Form ACC1, comprising:
   (i) dissolving Mitapivat hemi sulfate in a suitable solvent or solvent mixture;
   (ii) adding ascorbic acid;
   (iii) optionally adding an anti-solvent;
   (iv) precipitating crystalline Mitapivat hemi sulfate: ascorbic acid; and
   (v) optionally isolating crystalline Mitapivat hemi sulfate:ascorbic acid.

8. A process according to Clause 7, further comprising combining the crystalline product with at least one pharmaceutically acceptable excipient to provide a pharmaceutical composition, preferably wherein the pharmaceutical composition is a tablet or capsule.

9. A crystalline product obtainable by a process according to Clause 7.

10. A pharmaceutical composition comprising a crystalline product according to any of Clauses 1-6 or 9 and at least one pharmaceutically acceptable excipient.

11. Use of a crystalline product according to any of Clauses 1-6 or 9 for the preparation of a pharmaceutical composition and/or formulation, preferably wherein the pharmaceutical formulation is a tablet.

12. A process for preparing the pharmaceutical composition according to Clause 10, comprising combining a crystalline product according to any of Clauses 1-6 or 9 with at least one pharmaceutically acceptable excipient.

13. A crystalline product according to any of Clauses 1-6 or 9, or a pharmaceutical composition according to Clause 10, for use as a medicament.

14. A crystalline product according to any of Clauses 1-6 or 9, or a pharmaceutical composition according to claim 10, for use in the treatment of Pyruvate kinase deficiencies, thalassemia and sickle cell disease.

15. A method of treating Pyruvate kinase deficiencies, thalassemia and sickle cell disease, comprising administering a therapeutically effective amount of a crystalline product according to any of Clauses 1-6 or 9, or a pharmaceutical composition according to Clause 10, to a subject in need of the treatment.

16. Use of a crystalline product according to any of Clauses 1-6 or 9, in the preparation of another solid state form of Mitapivat hemi sulfate:ascorbic acid.

17. A process for preparing a solid state form of Mitapivat hemi sulfate:ascorbic acid comprising preparing any one or a combination of a crystalline product according to any one of Clauses 1-6 or 9, and converting it to another solid state form thereof.

18. Crystalline Mitapivat hemi sulfate:adipic acid.

19. Crystalline Mitapivat hemi sulfate:adipic acid, which is a co-crystal.

20. A crystalline product according to Clause 18 or 19, designated Form ACC2, which is characterized by data selected from one or more of the following:
   d. an XRPD pattern having peaks at 10.4, 11.0, 14.7, 16.2, and 16.6 degrees 2-theta±0.2 degrees 2-theta;
   e. an XRPD pattern as depicted in FIG. 2; and
   f. combinations of these data.

21. A crystalline product according to any of Clauses 18, 19, or 20, designated Form ACC2, characterized by the XRPD pattern having peaks at 10.4, 11.0, 14.7, 16.2, and 16.6 degrees 2-theta±0.2 degrees 2-theta, and also having one, two, three or four additional peaks selected from 8.7, 9.1, 17.6, 20.2, and 22.5 degrees two theta±0.2 degrees two theta.

22. A crystalline product according to any of Clauses 18, 19, 20, or 21, designated Form ACC2 which contains: no more than about 20%, no more than about 10%, no more than about 5%, no more than about 2%, no more than about 1% or about 0% of any other crystalline forms of Mitapivat hemi sulfate:adipic acid.

23. A crystalline product according to any of Clauses 18, 19, 20, 21, or 22, designated form ACC2, which contains: no more than about 20%, no more than about 10%, no more than about 5%, no more than about 2%, no more than about 1% or about 0% of amorphous Mitapivat hemi sulfate:adipic acid.

24. A process for the preparation of a crystalline product according to any of Clauses 18, 19, 20, 21, 22, or 23, designated Form ACC2, comprising:
   (i) dissolving Mitapivat hemi sulfate in a suitable solvent or solvent mixture;
   (ii) adding adipic acid;
   (iii) optionally adding an anti-solvent;
   (iv) precipitating crystalline Mitapivat hemi sulfate: adipic acid; and
   (v) optionally isolating crystalline Mitapivat hemi sulfate:adipic acid.

25. A process according to Clause 24, further comprising combining the crystalline product with at least one pharmaceutically acceptable excipient to provide a pharmaceutical composition, preferably wherein the pharmaceutical composition is a tablet or capsule.

26. A crystalline product obtainable by a process according to Clause 24.

27. A pharmaceutical composition comprising a crystalline product according to any of Clauses 18-23 or 26 and at least one pharmaceutically acceptable excipient.

28. Use of a crystalline product according to any of Clauses 18-23 or 26 for the preparation of a pharmaceutical composition and/or formulation, preferably wherein the pharmaceutical formulation is a tablet.

29. A process for preparing the pharmaceutical composition according to Clause 27, comprising combining a crystalline product according to any of Clauses 18-23 or 26 with at least one pharmaceutically acceptable excipient.

30. A crystalline product according to any of Clauses 18-23 or 26, or a pharmaceutical composition according to Clause 27, for use as a medicament.

31. A crystalline product according to any of Clauses 18-23 or 26, or a pharmaceutical composition according to claim 27, for use in the treatment of Pyruvate kinase deficiencies, thalassemia and sickle cell disease.

32. A method of treating Pyruvate kinase deficiencies, thalassemia and sickle cell disease, comprising administering a therapeutically effective amount of a crystalline product according to any of Clauses 18-23 or 26, or a pharmaceutical composition according to Clause 27, to a subject in need of the treatment.

33. Use of a crystalline product according to any of Clauses 18-23 or 26, in the preparation of another solid state form of Mitapivat hemi sulfate:adipic acid.

34. A process for preparing a solid state form of Mitapivat hemi sulfate:adipic acid comprising preparing any one or a combination of a crystalline product according to any one of Clauses 18-23 or 26, and converting it to another a solid state form thereof.

The invention claimed is:

1. A crystalline product of Mitapivat hemisulfate and an ascorbic acid co-former, wherein the crystalline product is characterized by an XRPD pattern having peaks at 8.9, 13.3, 14.9, 15.9, and 20.5 degrees 2-theta±0.2 degrees 2-theta.

2. A crystalline product according to claim 1, which is characterized by data selected from one or more of the following:
 a) an XRPD pattern as depicted in FIG. 5;
 b) an FTIR spectrum having peaks at 1765 cm$^{-1}$ and 1680 cm$^{-1}$±2 cm$^{-1}$;
 c) an FTIR spectrum as depicted in FIG. 16; or
 d) combinations of these data.

3. A crystalline product according to claim 2, designated Form ACC1, characterized by the XRPD pattern having peaks at 8.9, 13.3, 14.9, 15.9, and 20.5 degrees 2-theta±0.2 degrees 2-theta, and also having one, two, three or four additional peaks selected from 10.4, 10.7, 18.1, 18.7, and 23.1 degrees two theta±0.2 degrees two theta.

4. A process for the preparation of a crystalline product according to claim 2, comprising:
 (i) dissolving Mitapivat hemisulfate in a suitable solvent or solvent mixture;
 (ii) adding ascorbic acid;
 (iii) optionally adding an anti-solvent;
 (iv) precipitating crystalline Mitapivat hemisulfate:ascorbic acid; and
 (v) optionally isolating crystalline Mitapivat hemisulfate: ascorbic acid.

5. A process according to claim 4, further comprising combining the crystalline product with at least one pharmaceutically acceptable excipient to provide a pharmaceutical composition, preferably wherein the pharmaceutical composition is a tablet or capsule.

6. A crystalline product obtainable by a process according to claim 4.

7. A pharmaceutical composition comprising a crystalline product according to claim 2 and at least one pharmaceutically acceptable excipient.

8. A process comprising combining a crystalline product according to claim 2 with at least one pharmaceutically acceptable excipient.

9. A crystalline product of Mitapivat hemisulfate and an adipic acid co-former, wherein the crystalline product is characterized by an XRPD pattern having peaks at 10.4, 11.0, 14.7, 16.2, and 16.6 degrees 2-theta±0.2 degrees 2-theta.

10. A crystalline product according to claim 9, designated Form ACC2, which is characterized by data selected from one or more of the following:
 a) an XRPD pattern as depicted in FIG. 6;
 b) an FTIR spectrum having peaks at 1721 cm$^{-1}$ and 1638 cm$^{-1}$±2 cm$^{-1}$;
 c) an FTIR spectrum as depicted in FIG. 20; or
 d) combinations of these data.

11. A crystalline product according to claim 10, designated Form ACC2, characterized by the XRPD pattern having peaks at 10.4, 11.0, 14.7, 16.2, and 16.6 degrees 2-theta±0.2 degrees 2-theta, and also having one, two, three or four additional peaks selected from 8.7, 9.1, 17.6, 20.2, and 22.5 degrees two theta±0.2 degrees two theta.

12. A process for the preparation of a crystalline product according to claim 9, designated Form ACC2, comprising:
 (i) dissolving Mitapivat hemi sulfate in a suitable solvent or solvent mixture;
 (ii) adding adipic acid;
 (iii) optionally adding an anti-solvent;
 (iv) precipitating crystalline Mitapivat hemi sulfate:adipic acid; and
 (v) optionally isolating crystalline Mitapivat hemi sulfate: adipic acid.

13. A process according to claim 12, further comprising combining the crystalline product with at least one pharmaceutically acceptable excipient to provide a pharmaceutical composition, preferably wherein the pharmaceutical composition is a tablet or capsule.

14. A crystalline product obtainable by a process according to claim 13.

15. A pharmaceutical composition comprising a crystalline product according to claim 9 and at least one pharmaceutically acceptable excipient.

16. A process comprising combining a crystalline product according to claim 9 with at least one pharmaceutically acceptable excipient.

* * * * *